US012612343B2

(12) United States Patent
Song et al.

(10) Patent No.: US 12,612,343 B2
(45) Date of Patent: Apr. 28, 2026

(54) PSMA BINDER AND USE THEREOF

(71) Applicant: SHIYA PHARMACEUTICAL, INC., Shanghai (CN)

(72) Inventors: Shaoli Song, Shanghai (CN); Xiaoping Xu, Shanghai (CN); Chang Liu, Shanghai (CN)

(73) Assignee: SHIYA PHARMACEUTICAL, INC, Shanghai (CN)

( * ) Notice: Subject to any disclaimer, the term of this patent is extended or adjusted under 35 U.S.C. 154(b) by 712 days.

(21) Appl. No.: 17/642,179

(22) PCT Filed: Apr. 13, 2021

(86) PCT No.: PCT/CN2021/086783

§ 371 (c)(1),
(2) Date: Mar. 10, 2022

(87) PCT Pub. No.: WO2021/175338

PCT Pub. Date: Sep. 10, 2021

(65) Prior Publication Data

US 2022/0315507 A1 Oct. 6, 2022

(30) Foreign Application Priority Data

Mar. 3, 2020 (CN) ......................... 202010140466.7

(51) Int. Cl.

| | |
|---|---|
| ***C07B 59/00*** | (2006.01) |
| ***A61K 51/04*** | (2006.01) |
| ***A61P 35/04*** | (2006.01) |
| ***C07K 5/072*** | (2006.01) |

(52) U.S. Cl.
CPC ........ *C07B 59/008* (2013.01); *A61K 51/0455* (2013.01); *A61P 35/04* (2018.01); *C07K 5/06113* (2013.01)

(58) Field of Classification Search
CPC .... C07B 59/008; A61P 35/04; A61K 51/0455
USPC ........................................................ 424/1.69
See application file for complete search history.

(56) References Cited

U.S. PATENT DOCUMENTS

2020/0324000 A1* 10/2020 Sikora ...................... A61K 9/19

FOREIGN PATENT DOCUMENTS

| | | | | | |
|---|---|---|---|---|---|
| CN | 108026144 | A | | 5/2018 | |
| CN | 109641924 | A | | 4/2019 | |
| CN | 109982722 | A | | 7/2019 | |
| CN | 111253465 | A | * | 6/2020 | ......... C07K 5/06113 |
| CN | 111777663 | A | | 10/2020 | |
| WO | WO-2017054907 | A1 | * | 4/2017 | ........... A61K 31/465 |
| WO | 2019175405 | A1 | | 9/2019 | |

OTHER PUBLICATIONS

Ferro-Flores et al. Nucl. Med. Biol. 48 (2017) 36-44. (Year: 2017).*
Liu et al. Dalton Trans. 2011, 40, 6077-6086. (Year: 2011).*

* cited by examiner

*Primary Examiner* — Michael G. Hartley
*Assistant Examiner* — Sean R Donohue
(74) *Attorney, Agent, or Firm* — IPRTOP LLC

(57) ABSTRACT

The present invention discloses a prostate specific membrane antigen (PSMA) binding compound, a radioactive isotope complex thereof, and the use thereof in nuclear medicine as a tracer and an imaging agent for different disease states of prostate cancer.

13 Claims, 10 Drawing Sheets

PSMA BINDER AND USE THEREOF

CROSS REFERENCE TO RELATED PATENT APPLICATION

The present application is the US national stage of PCT/2021/086783 filed on 2021 Apr. 13, which claims the priority of the Chinese patent application No. 202010140466.7 filed on 2020 Mar. 3, which application is incorporated herein by reference.

FIELD OF TECHNOLOGY

The present invention relates to a radioisotope-labeled prostate specific membrane antigen (PSMA) binding compound, and precursor compounds thereof. The compound is applied as a tracer and an imaging agent in nuclear medicine to visualized various disease states of prostate cancer.

BACKGROUND

Prostate cancer (PCa) is the second most common cancer for men worldwide, and its mortality rate ranks fifth among male cancers. There were nearly 400,000 deaths worldwide due to PCa in 2018. Metastasis, recurrence, and resistance to androgen therapy are the leading causes of death for prostate cancer patients. Currently, there is a lack of effective diagnostic methods and therapeutic regimens for metastatic, recurrent and androgen therapy-resistant prostate cancer. Traditional anatomical imaging methods such as computed tomography (CT), magnetic resonance (MR) imaging, and ultrasound all have significant defects. Molecular imaging allows understanding of tumor physiology at the molecular level, enabling more precise prognosis and efficacy monitoring. $^{18}$F-labeled deoxyglucose (FDG) is the most commonly used clinical molecular imaging probe, but $^{18}$F-FDG PET/CT has limited diagnostic value for PCa due to the relatively low metabolism of PCa.

At present, other radioactive molecular imaging tracers are being explored clinically to detect PCa, including radiolabeled choline drugs ($^{11}$C-choline), radiolabeled acetate ($^{11}$C-acetate), radiolabeled testosterone ($^{18}$F-FDHT), anti-1-amino-3-[$^{18}$F]fluorocyclobutane-1-carboxylic acid ($^{18}$F-FACBC) and 1-(2-deoxy-2-[$^{18}$F]-fluoro-L-arabinofuranosyl)-5-thymine ($^{18}$F-FMAU) and the like. They each reflect prostate cancer status through different mechanisms, but none of them is ideal (i.e., easy to synthesis, minimal urinary metabolism, and with tumor-specific uptake).

Prostate specific membrane antigen (PSMA) is a protein that is highly specifically expressed on the surface of prostate cancer cells, and its expression is further elevated in metastatic hormone-resistant PCa. Due to metastatic hormone-resistant PCa has a high degree of malignancy, poor prognosis, and is an inevitable stage of PCa development, PSMA is an excellent target in the diagnosis and treatment of PCa. ProstaScint®, which has been successfully marketed, is a monoclonal antibody nuclide imaging agent targeting PSMA. It was approved for prostate cancer imaging by the US Food and Drug Administration (FDA) in the 1990s. However, binding sites of ProstaScint® and PSMA are located in the cell membrane and ProstaScint® mainly binds to the necrotic parts of the tumor rather than the viable tumor cells, therefore, ProstaScint® has not been promoted.

Recent studies have shown that a class of small-molecule compounds constructed based on glutamate-urea-glutamate (GUG) or glutamate-urea-lysine (GUL) exhibit high affinity for PSMA, which can be used in the diagnosis and treatment of prostate cancer with the help of various radionuclides. Some compounds such as $^{68}$Ga-PSMA1, $^{18}$F-DCFPyL, $^{18}$F-FDCBC, $^{99m}$Tc-MIP-1404, $^{99m}$Tc-HYNIC-ALUG and the like are currently undergoing clinical experimental research. However, these compounds are all or partially excreted from the urinary system, which will affect the diagnosis of primary tumor of PCa and local recurrence of prostate after surgery.

SUMMARY

The present invention provides new tissue-specific compounds for prostate cancer, and the use thereof in nuclear medicine as imaging agents and tracers for PCa. In particular, the present invention provides an imaging agent different from that of the prior art in terms of modification, wherein the imaging agent is not known or not recommended previously. The present invention avoids excretion of the imaging agent from urinary system, and tumor from being covered by high intake bladder.

The present invention relates to a compound represented by the following general formula (I):

general formula I

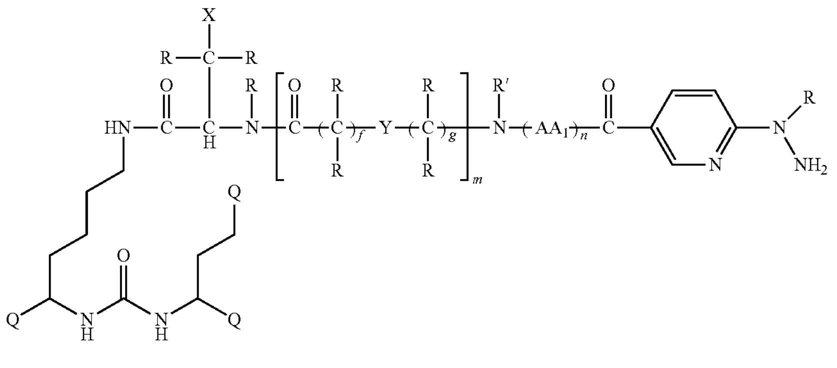

wherein:

m is an integer from 0 to 5;

n is an integer from 0 to 5;

f and g each is 0 or 1;

R and R' each is independently selected from H, alkyl, halogen, —CN, —OH, —$NH_2$, alkoxy or cycloalkyl;

Q is —COOH, —SOON, —$SO_3H$, —$SO_4H$, —POOH, —$PO_3H$ or —$PO_4H_2$;

X is an optionally substituted aryl or an optionally substituted heteroaryl, which is substituted by at least one R group;

Y is an optionally substituted aryl, an optionally substituted heterocyclic aryl, an optionally substituted cycloalkyl, or an optionally substituted heterocycloalkyl, which is substituted by at least one R group;

$AA_1$ is a natural or non-natural amino acid, or $—CH_2CH_2—$.

Further, the formula (I) is a compound represented by formula (I-1):

(I-1)

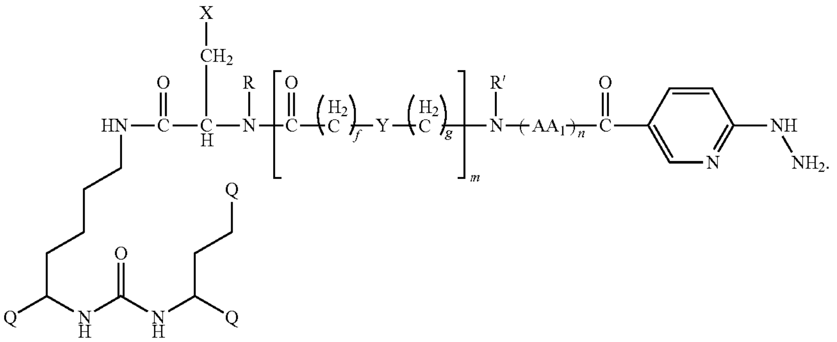

Further, the R and R' each is independently selected from H and $C_1$-$C_{10}$ alkyl;

the X is an optionally substituted phenyl, naphthyl, biphenyl, indolyl, benzothiazolyl or quinolinyl;

the optionally substituted heterocycloalkyl is selected from N-piperidinyl or N-methylated piperidinium.

The present invention further provides a radionuclide complex, which can be used in SPECT/CT imaging of a target tissue.

Specifically, the radionuclide complex comprises a radionuclide and a PSMA small molecule inhibitor, where the PSMA small molecule inhibitor has a structure represented by formula (II):

(II)

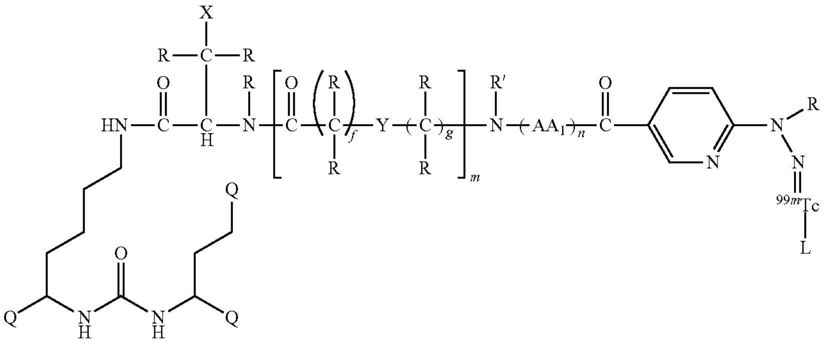

where Q, R, X, f, Y, g, m, R', $AA_1$ and n are as defined above,

L is N-tris(hydroxymethyl)methylglycine, ethylenediamine-N,N'-diacetic acid, triphenylphosphine-3,3',3''-trisulfonic acid trisodium, disodium 3,3'-(phenylphosphinediyl)bis(benzene-1-sulphonate), sodium diphenylphosphinobenzene-3-sulfonate, nicotinic acid, glucoheptonate, glucosamine, mannitol, or diphenylphosphinobenzoic acid.

Further, the complex is a compound represented by formula (II-1):

Formuyla (II-1)

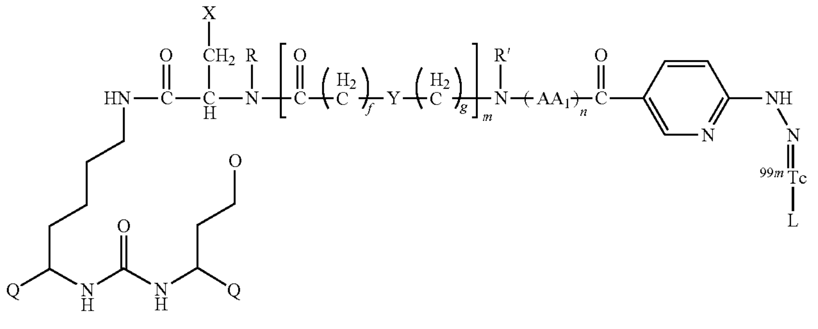

Unless otherwise stated, the term "alkyl" itself or as part of another molecule in the present invention is a straight-chain or branched or cyclic hydrocarbyl group, or a combination thereof, which can be fully saturated, monounsaturated or polyunsaturated, and can include a bivalent and multivalent group. An "alkyl" residue is preferably C1 to C10 and may be unsubstituted or substituted (e.g., substituted with a halogen). A preferred alkyl residue is methyl, ethyl, n-propyl, isopropyl, n-butyl, tert-butyl, n-pentyl, n-hexyl, n-heptyl or n-octyl or the like. This is also applicable to a corresponding cycloalkyl compound having 3 to 10 carbon atoms, such as cyclopropyl, cyclobutyl, cyclopentyl, cyclohexyl, cycloheptyl, cyclooctyl, and the like. An unsaturated alkyl is an alkyl group having one or more double bonds or triple bonds. Examples of the unsaturated alkyl includes, but are not limited to, vinyl, 2-propenyl, 2-butenyl, 2-isopentenyl, 2-(butadienyl), 2,4-pentadienyl, 3-(1,4-pentadienyl), ethynyl, 1-propynyl and 3-propynyl, 3-butynyl, and advanced homologs and isomers. Unless otherwise stated, the term "alkyl" is also used to include those derivatives of alkyl, such as "heteroalkyl", "haloalkyl" and "advanced alkyl".

As used herein, the term "aryl" refers to a closed ring structure, which has at least one ring having a conjugated 7-electron system and includes a carbocyclic aryl group and a heterocyclic aryl (or "heteroaryl" or "heteroaromatic") group. A carbocyclic group or a heterocyclic aromatic group may contain 5 to 20 ring atoms. The above term includes covalently linked monocyclic or condensed polycyclic (i.e., a ring that shares an adjacent pair of carbon atoms) group. The aromatic group can be unsubstituted or substituted. Non-limiting examples of "aromatic" or "aryl" groups include phenyl, 1-naphthyl, 2-naphthyl, 2-biphenylyl, 3-biphenylyl, 4-biphenylyl, anthryl and phenanthryl. The substituents for each of the above aryl and heteroaryl ring systems are selected from the acceptable substituents (e.g., alkyl, carbonyl, carboxyl, or halogen) described herein. When used together with other terms (including but not limited to aryloxy, arylthiooxy, and aralkyl), the term "aryl" includes aryl and heteroaryl ring. Thus, the term "aralkyl" or "alkaryl" is used to include those groups in which the aryl group is attached to the alkyl group (including but not limited to benzyl, phenethyl, pyridylmethyl, etc.), the alkyl group includes those whose carbon atoms (including but not limited to methylene) have been replaced by heteroatoms, or by oxygen atoms for illustration only. Examples of such aryl groups include, but are not limited to, phenoxymethyl, 2-pyridyloxymethyl, 3-(1-naphthyloxy)propyl, and the like.

"Heteroaryl" refers to an aryl group containing at least one heteroatom selected from N, O, and S, wherein the nitrogen and sulfur atoms may be optionally oxidized, and the nitrogen atom may be optionally quaternized. The heteroaryl group can be substituted or unsubstituted. The heteroaryl group can be attached to the remaining part of a molecule through a heteroatom. Non-limiting examples of suitable groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 4-benzothiazolyl, 5-benzothiazolyl, 6-benzothiazolyl, 7-benzothiazolyl, purinyl, 2-benzimidazolyl, 4-indolyl, 5-indolyl, 6-indolyl, 7-indolyl, 1-isoquinolinyl, 5-isoquinolinyl, 2-quinoxalinyl, 5-quinoxalinyl, 2-quinolinyl, 3-quinolinyl, 4-quinolinyl, 5-quinolinyl, 6-quinolinyl, 7-quinolinyl or 8-quinolinyl.

The term "amino acid" refers to natural amino acids and unnatural amino acids, as well as amino acid analogs and amino acid mimetics that act in a manner similar to natural amino acids. Natural amino acids are the 20 common amino acids in their D- or L-forms (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine) and pyrrolysine and selenocysteine. Amino acid analogs refer to compounds that have the same basic chemical structure as natural amino acids, for example, ex-carbon, which binds to hydrogen, carboxyl, amino and R groups. Such analogs can have modified R groups (for example, norleucine) or can have modified peptide backbones, while still remaining the same basic chemical structure as natural amino acids. Non-limiting examples of amino acid analogs include homoserine, norleucine, methionine sulfoxide and methionine methyl sulfonium. Amino acids may be referred to herein by their names, by their commonly known three-letter symbols, or by one-letter symbols (as recommended by the IUPAC-IUB Biochemical Nomenclature Committee). "Unnatural amino acid" refers to an amino acid that is not one of the 20 common amino acids or pyrrolysine or selenocysteine. Other terms that may be used synonymously with the term "unnatural amino acid" are "non-naturally encoded amino acid", "non-natural amino acid", "non-naturally occurring amino acid", or "artificial amino acid". The term "unnatural amino acid" includes, but is not limited to, amino acids which are produced by modifying naturally encoded amino acids in their backbones or side chains. In some embodiments, the unnatural amino acid comprises carbonyl group, acetyl group, aminooxy group, hydrazine group, hydrazide group, semicarbazide group, azide group, or alkynyl group. In an embodiment, $AA_1$ has the following chemical formula:

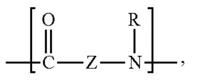

wherein

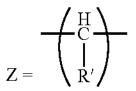

and R'═H, COOH, $CH_2COOH$, $C_2H_4COOH$, $CH(COOH)_2$, $CH(CH_2COOH)_2$, $CH(COOH)(CH_2COOH)$, $CH_2CH(COOH)_2$, or $SO_3H$;

i=1-3; and R═H or $CH_3$.

In an embodiment, amino acids bring hydrophilic elements into the compounds of general formula I.

Some residues herein (including but not limited to unnatural amino acids) may exist in several tautomeric forms. All such tautomeric forms are considered as part of the compounds described herein. Additionally, all enol-keto forms of any compound herein are considered as part of the compositions described herein.

$AA_1$, i.e., a natural amino acid and/or non-naturally occurring amino acid, can be bound intramolecularly through a peptide or amide bond. However, in the case of an acidic amino acid (e.g., glutamic acid or aspartic acid), the binding sites may alternatively be at the alpha-, beta- or gamma-position.

Although it is preferred that the Z group is —COOH, it can be easily replaced by biosteric substitutes such as $—SO_2H$, $—SO_3H$, $—SO_4H$, $—PO_2H$, $—PO_3H$, $—PO_4H_2$. See e.g. "The Practice of Medicinal Chemistry" (Academic Press New York, 1996), page 203.

Within the present invention, all residues are considered to be combinable unless otherwise stated in the definition of the residues. Conceivable subgroups of the residues are believed to be disclosed.

In the present invention, all chiral C atoms have the D- and/or L-configuration; furthermore, combinations within one compound are possible, i.e., some chiral C atoms may be in the D-configuration and the other chiral C atoms may be in the L-configuration.

The compound represented by formula (I) provided by the present invention can be selected from, but not limited to, the compounds having the following structures:

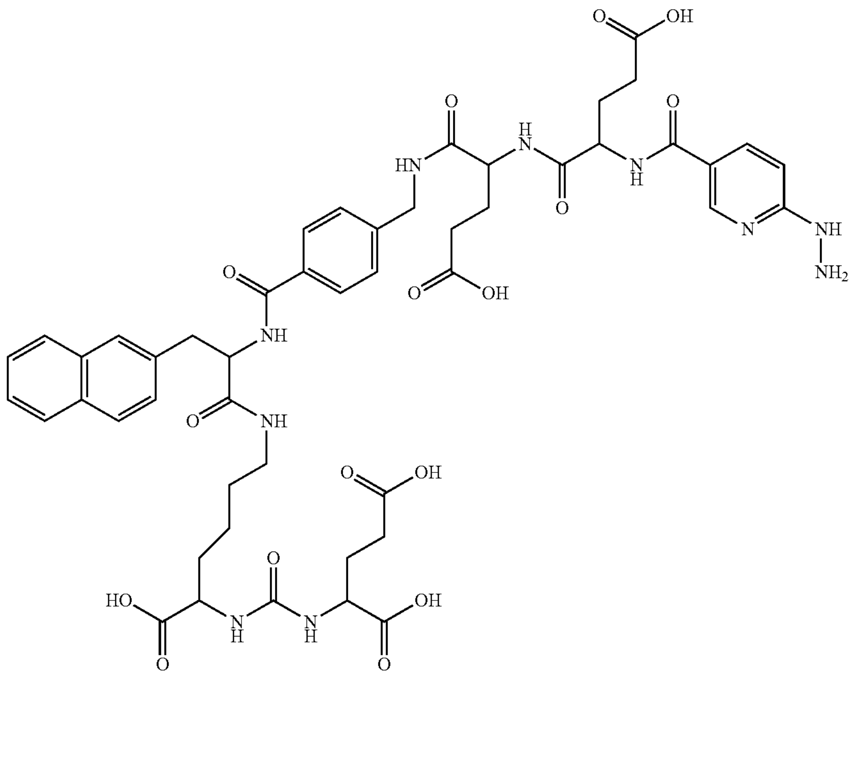

-continued
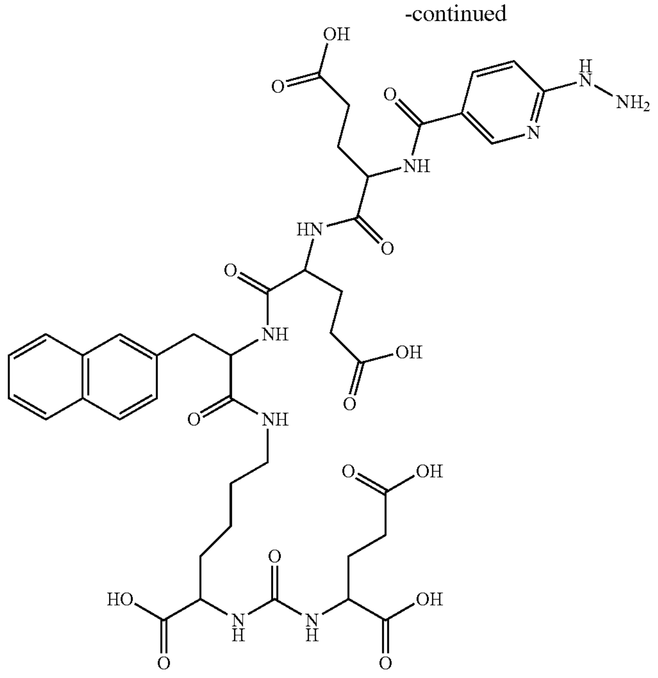
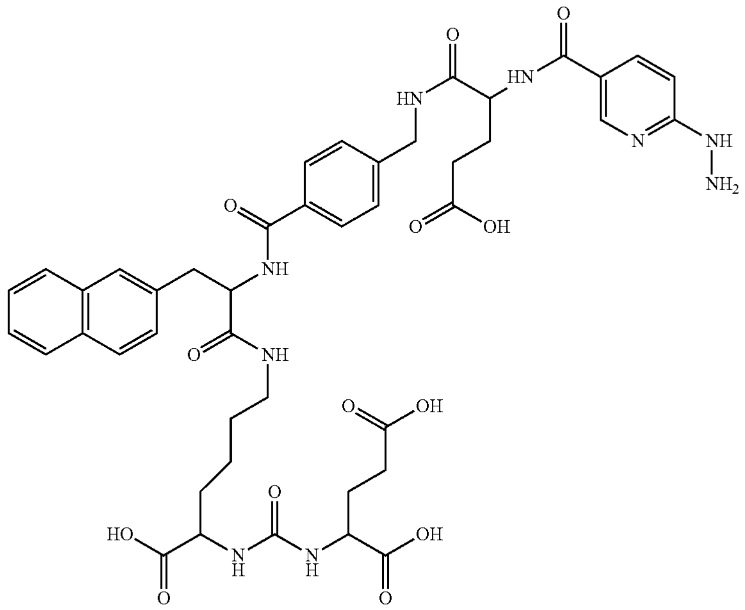

-continued
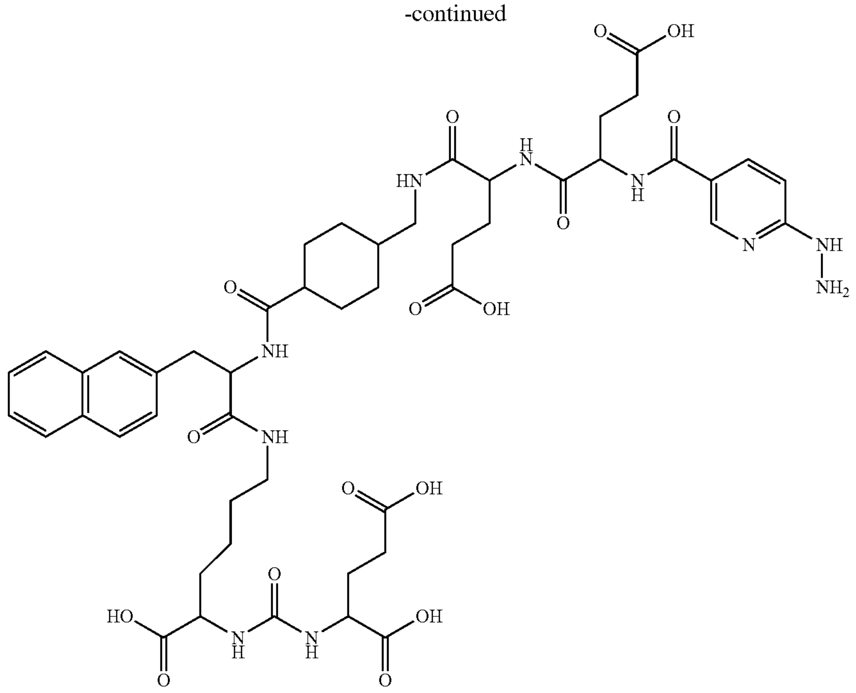
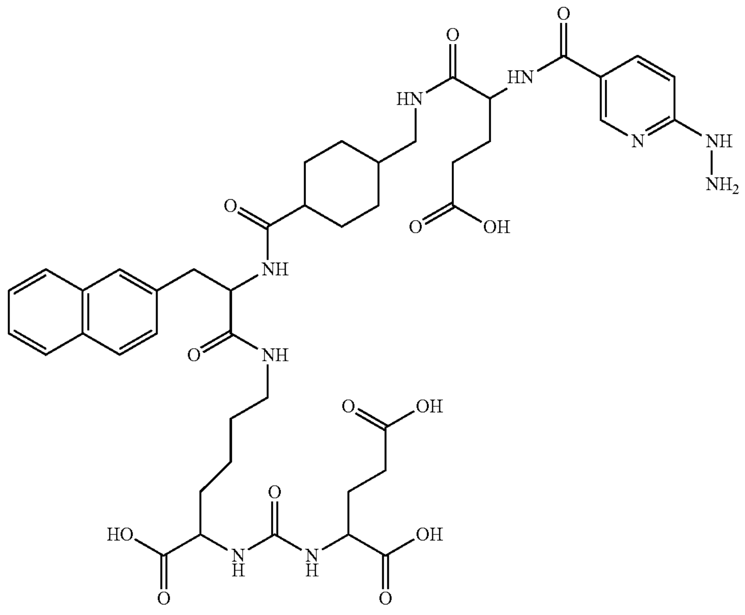

-continued
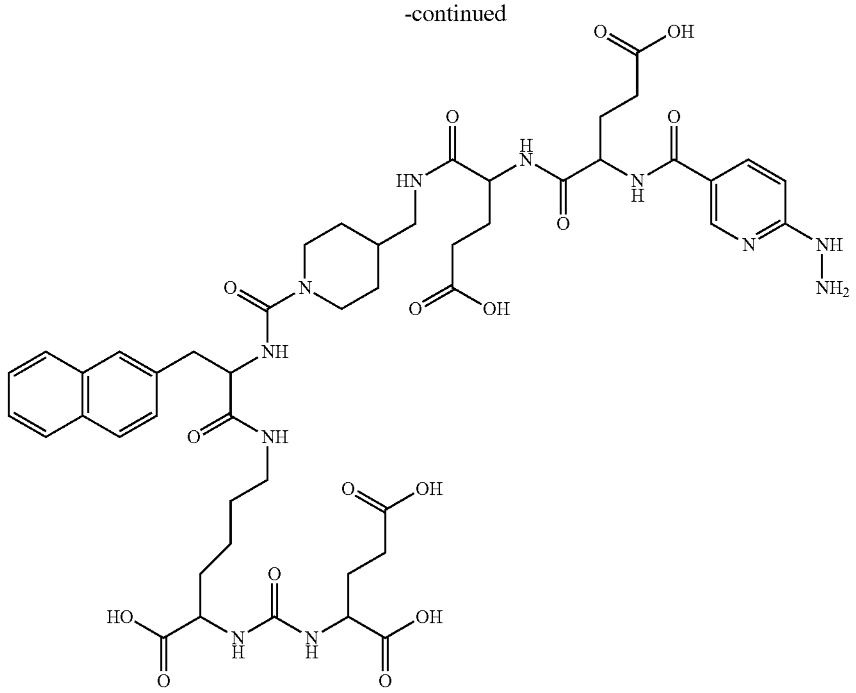
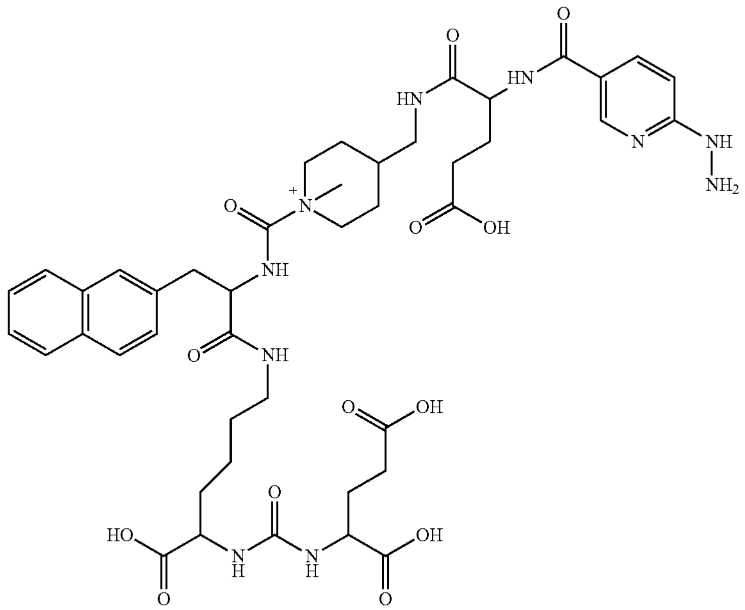

-continued
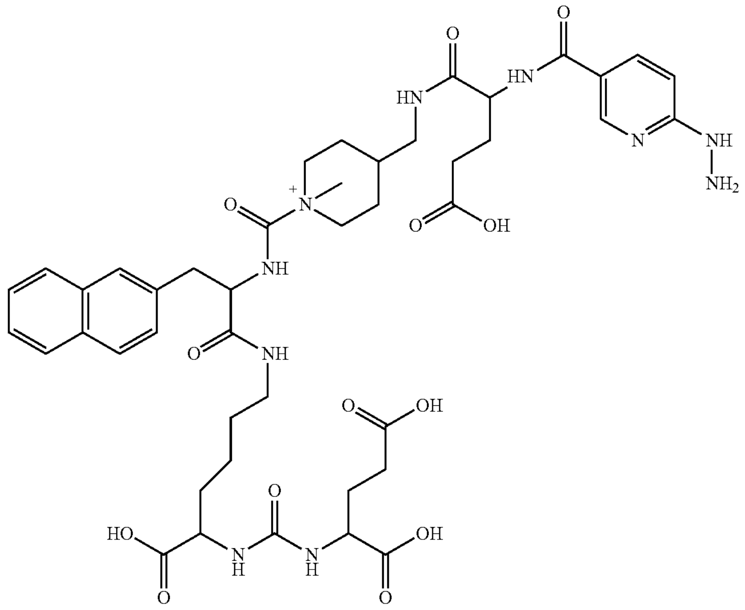
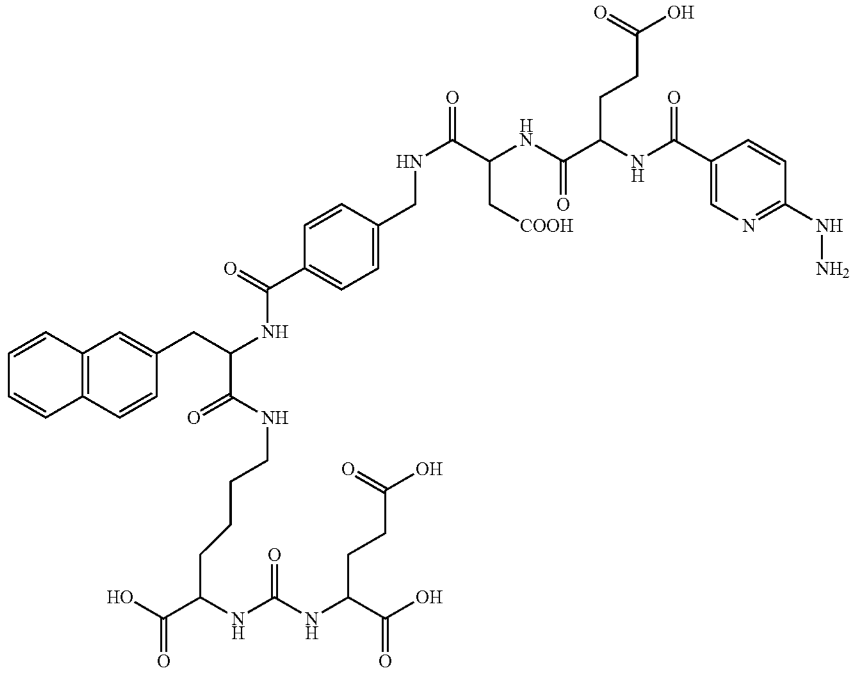

-continued
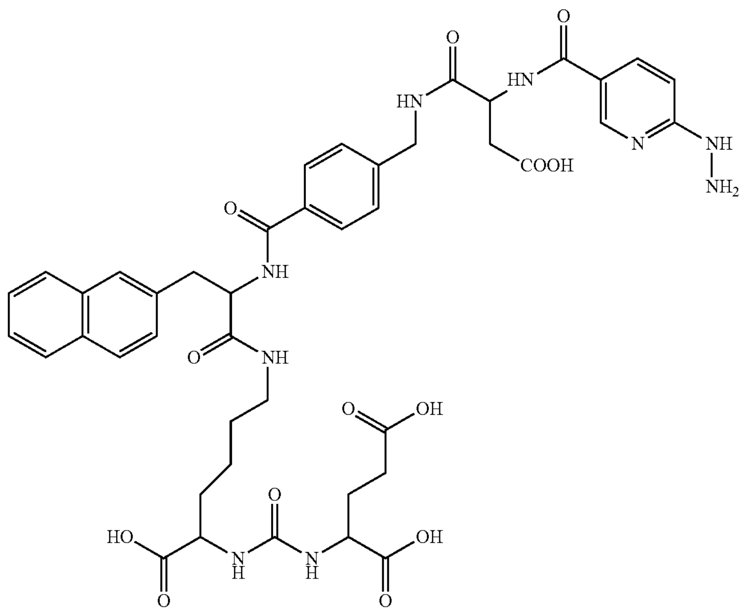
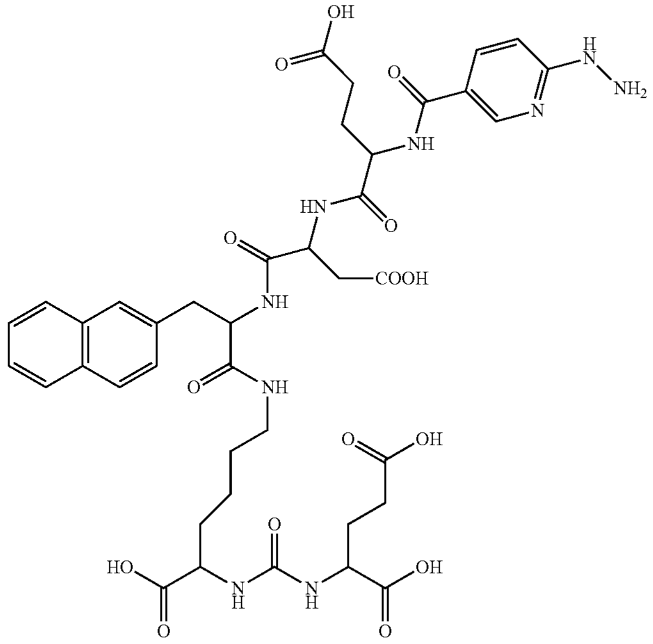

-continued
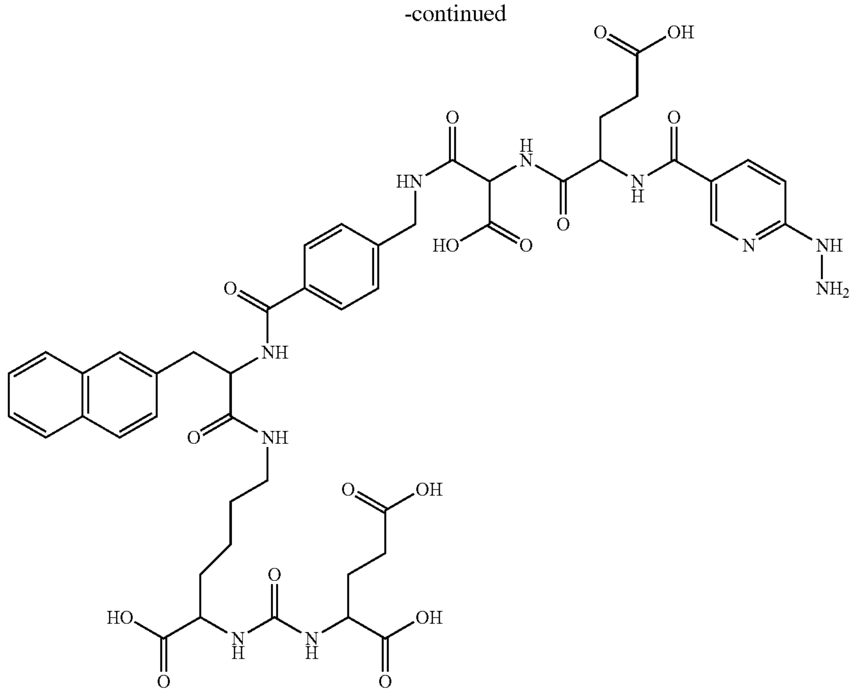
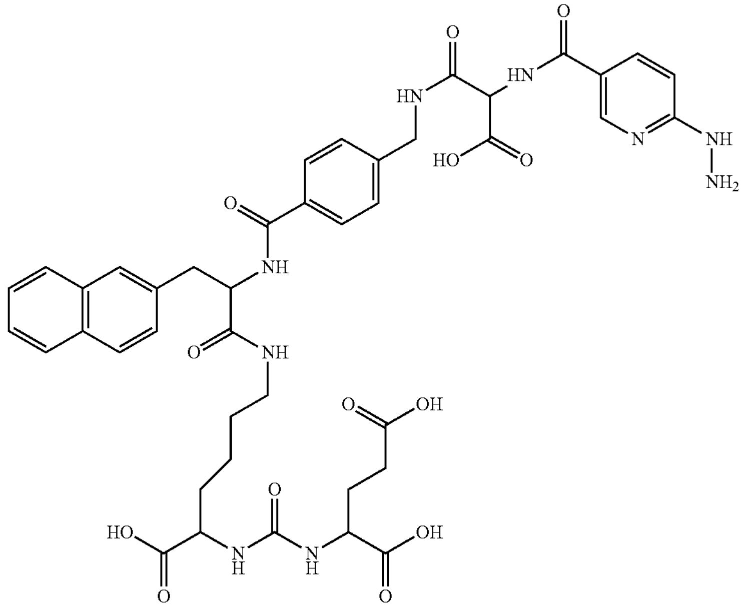

-continued
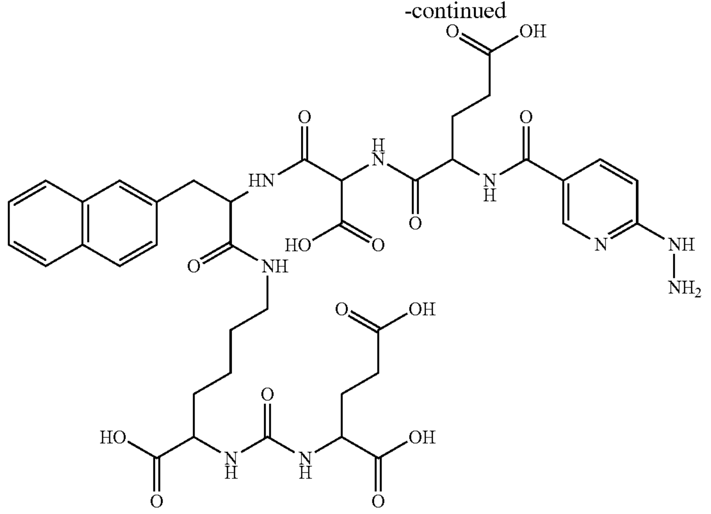
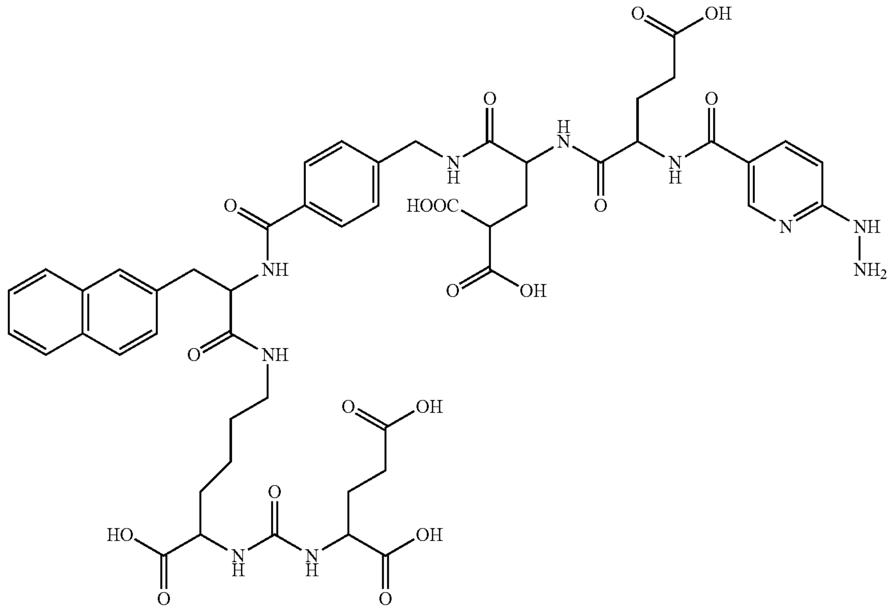
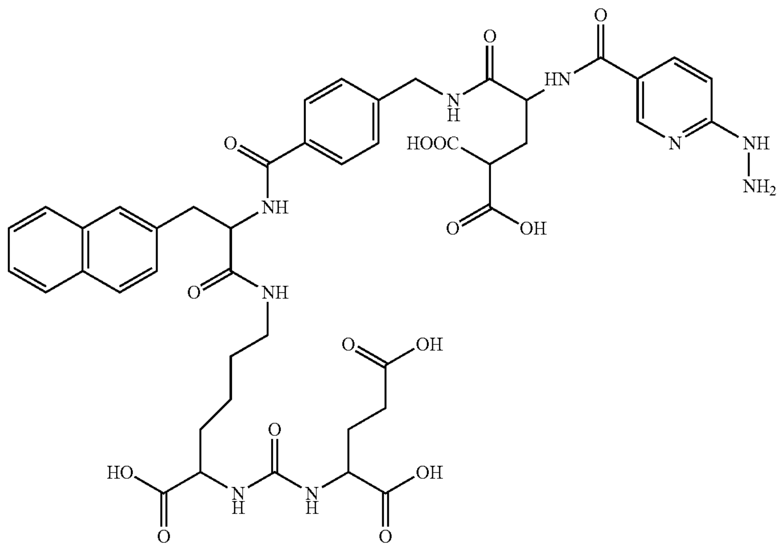 [SMILES: NNc1ccc(C(=O)NC(CC(C(=O)O)C(=O)O)C(=O)NCC2CCC(C(=O)NC(Cc3ccc4ccccc4c3)C(=O)NCCCCC(NC(=O)NC(CCC(=O)O)C(=O)O)C(=O)O)CC2)cn1]

-continued
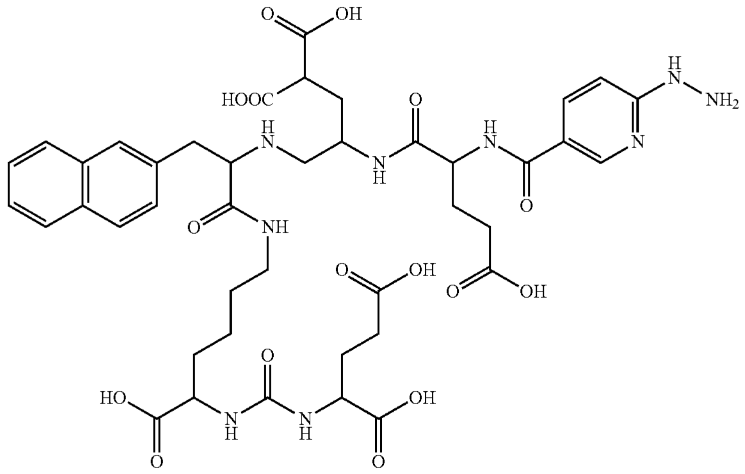
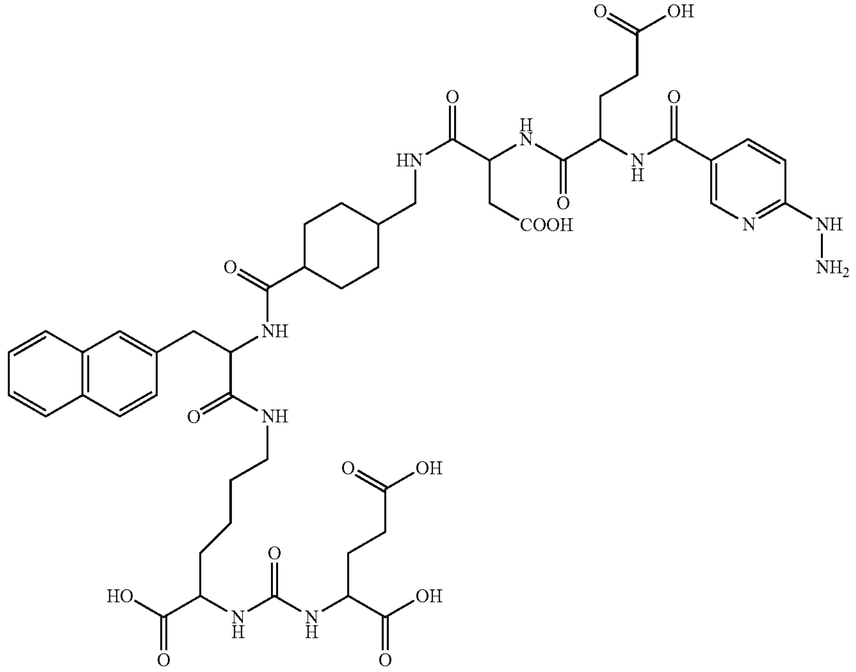

-continued
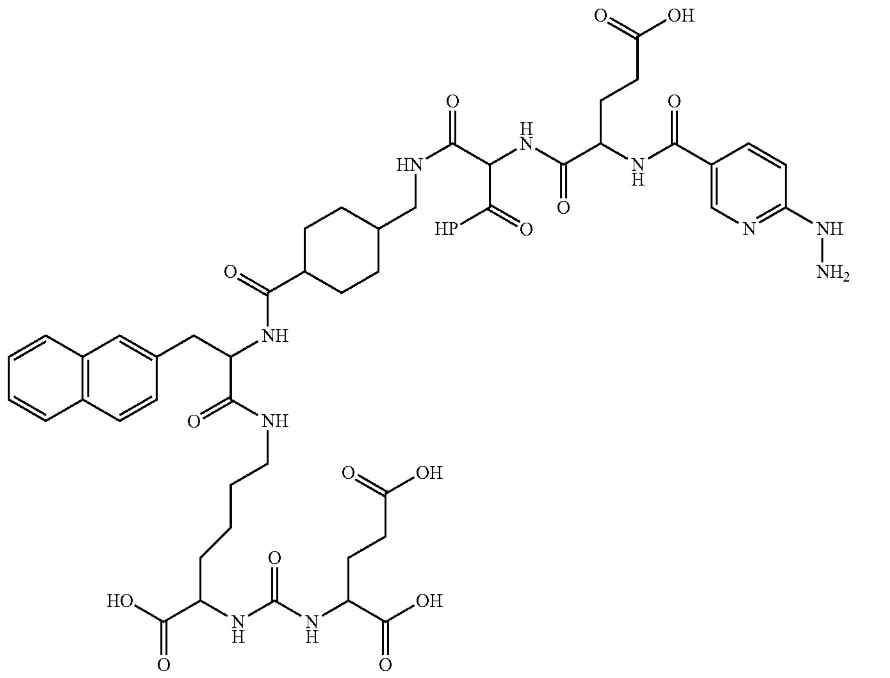
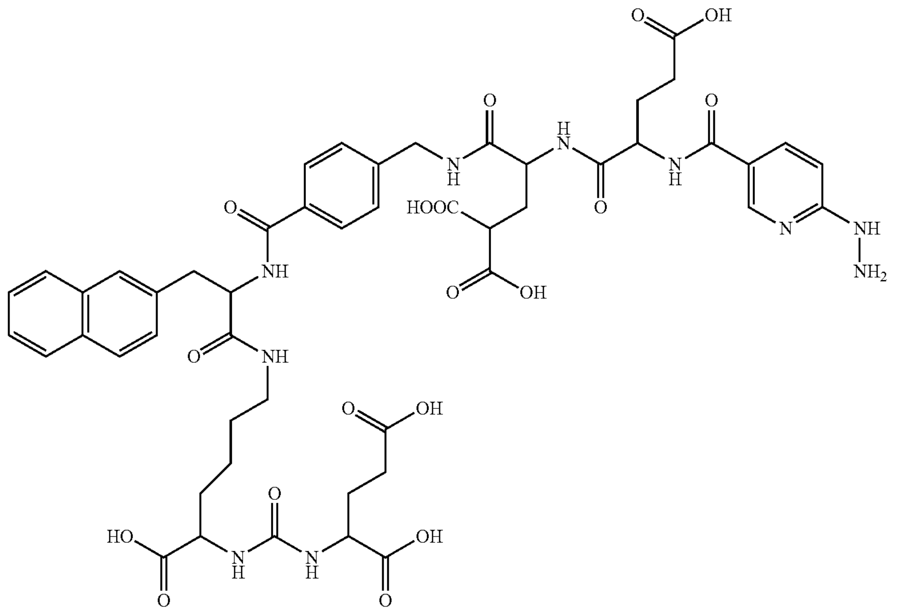

-continued
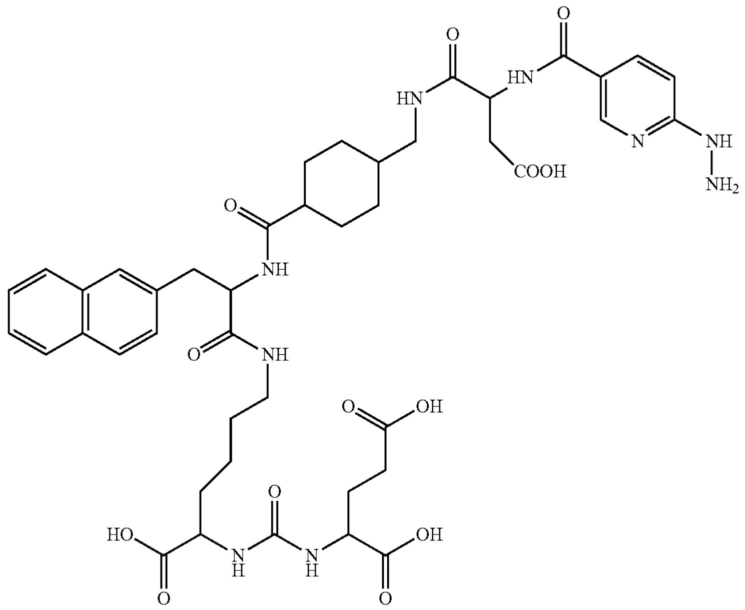
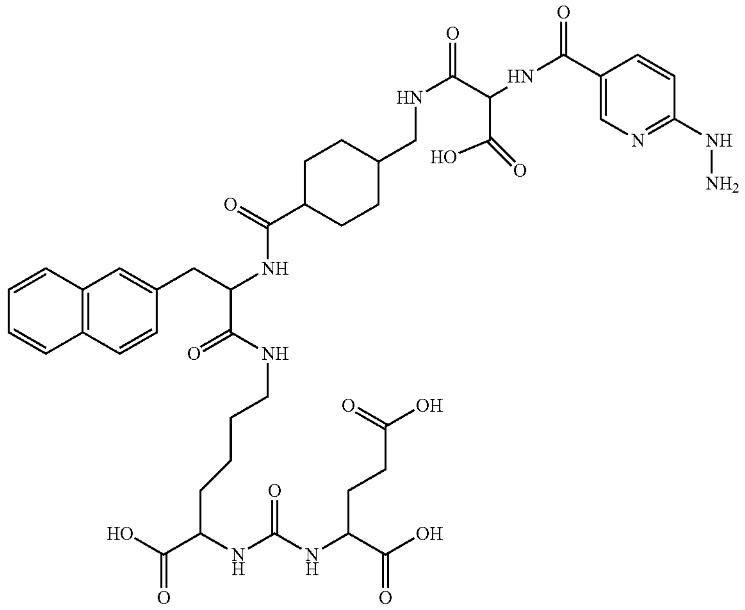

-continued
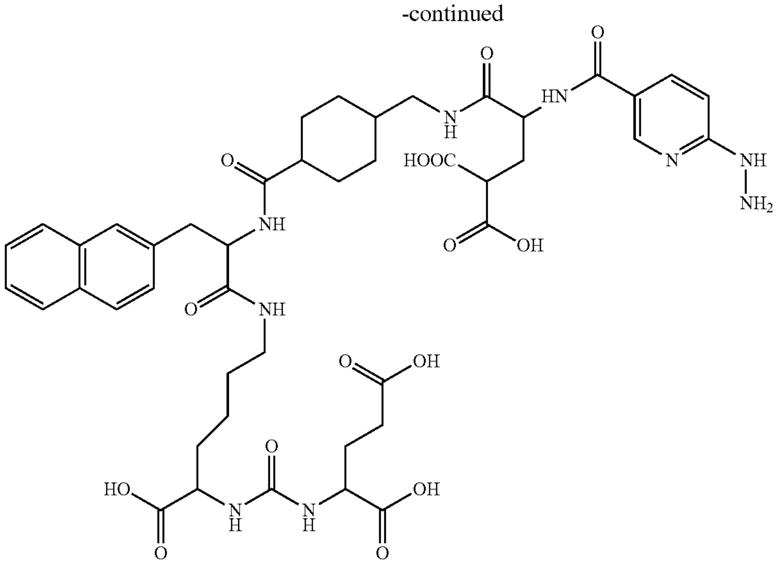
The complex of formula (II) provided by the present invention can be selected from, but not limited to, the complexes having the following structures:
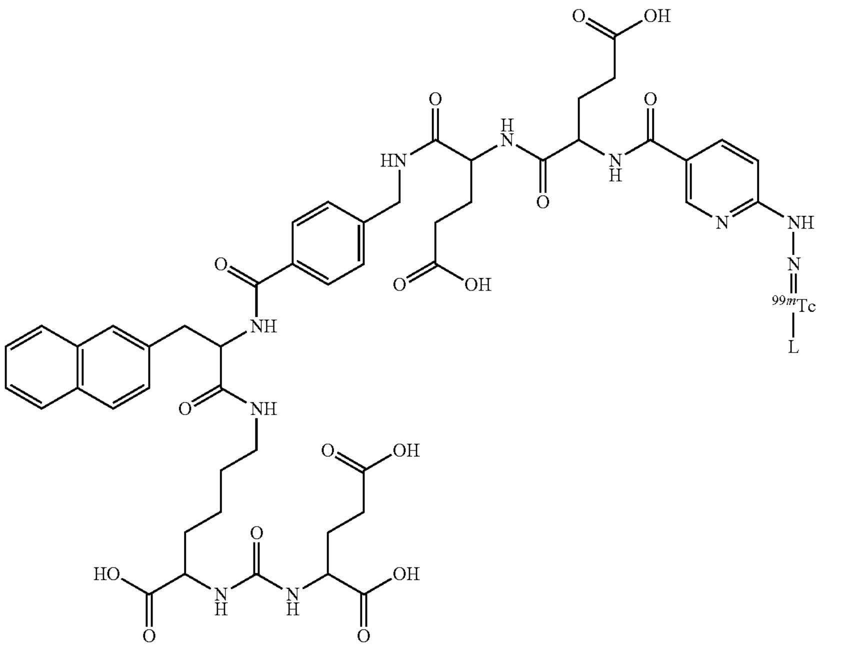
or -continued
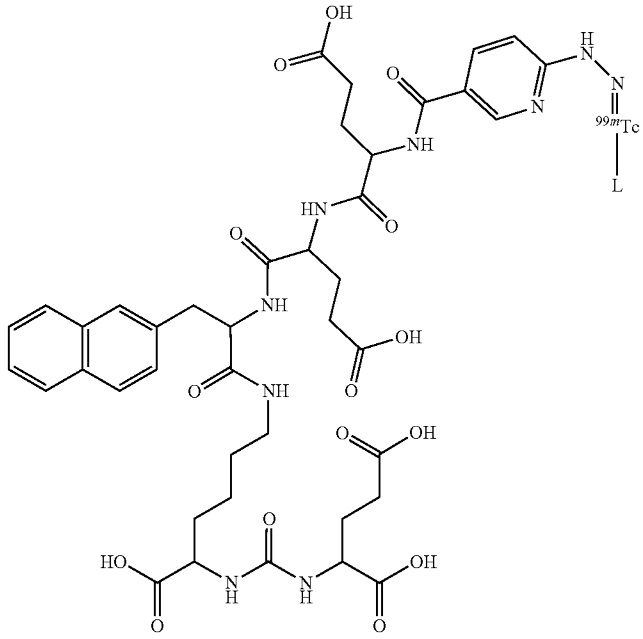
or
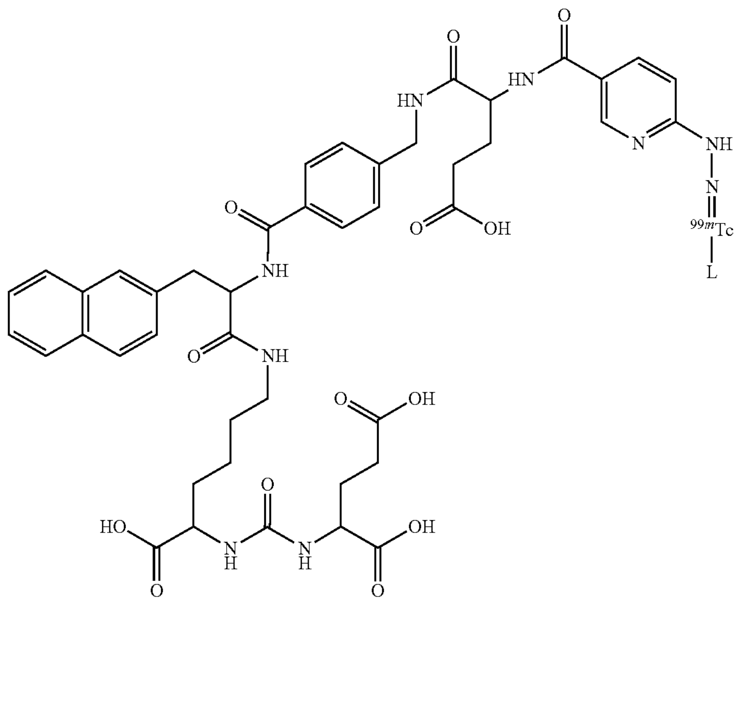
or -continued
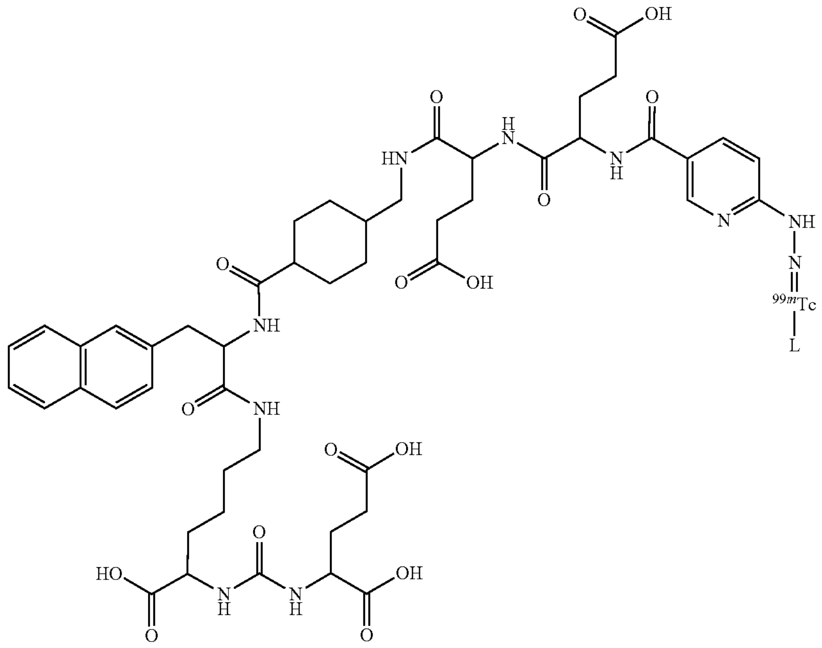
or
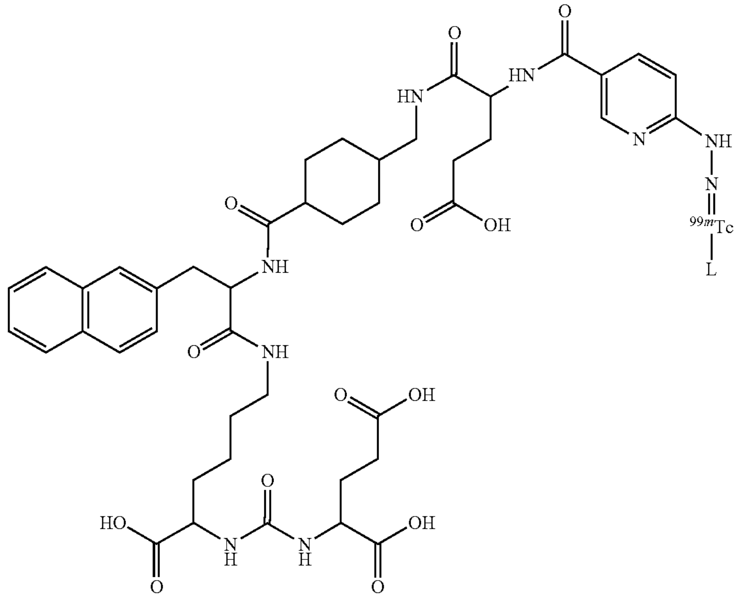
or -continued
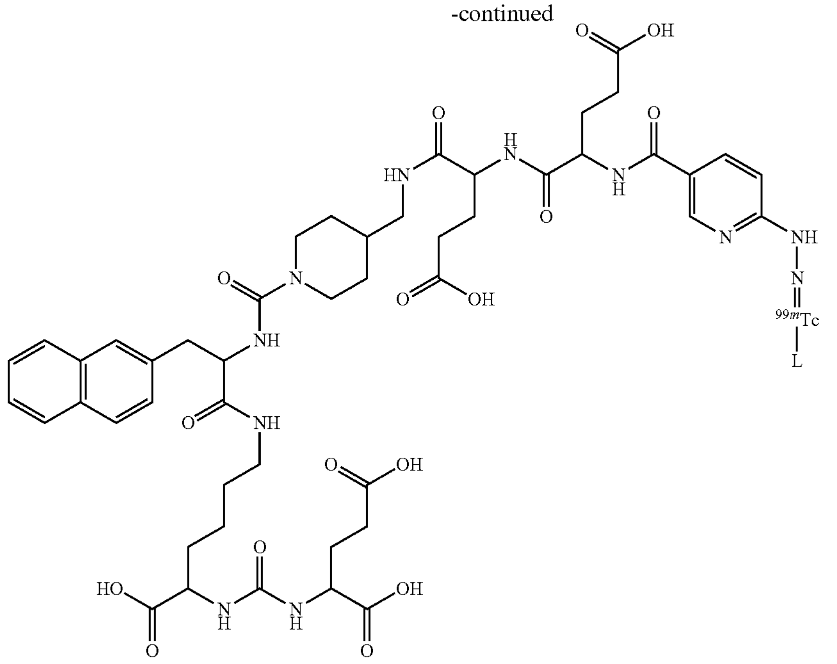
or
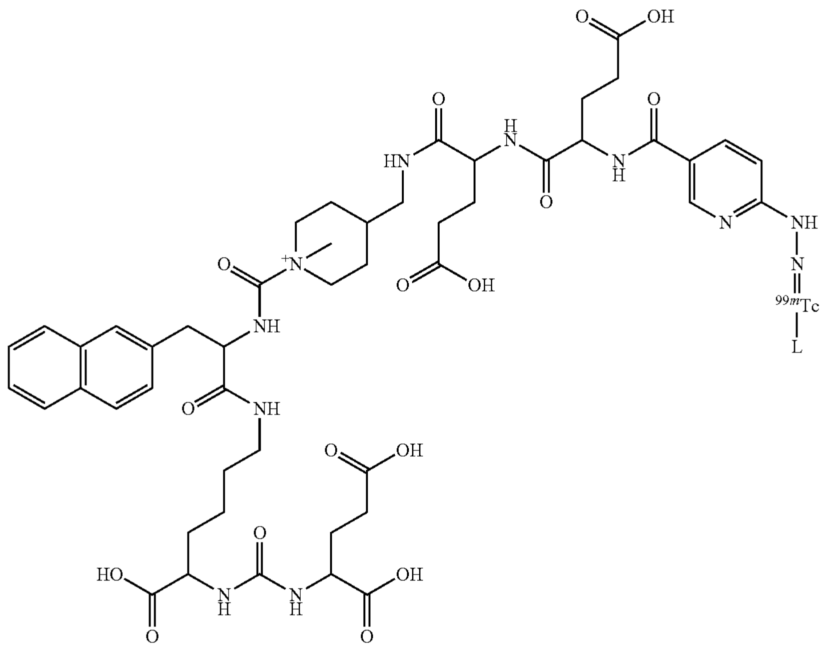
or -continued
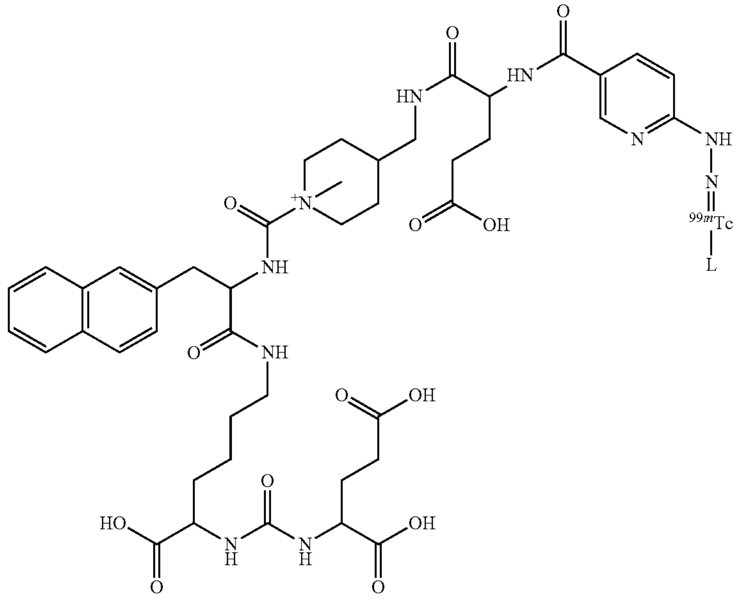
or
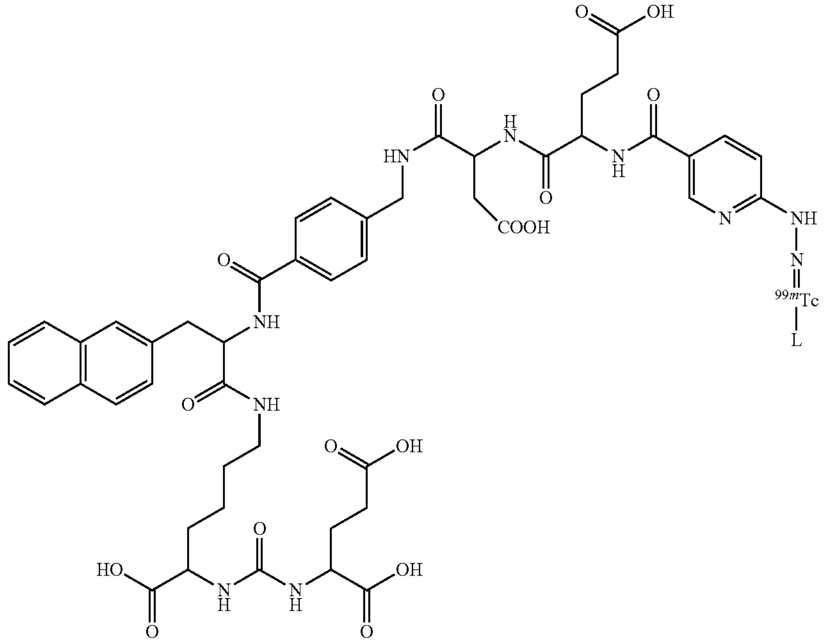
or -continued
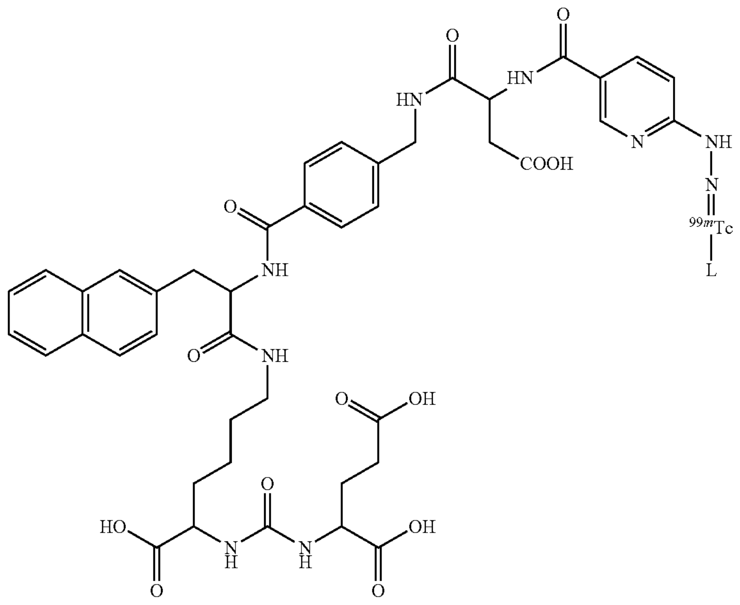
or
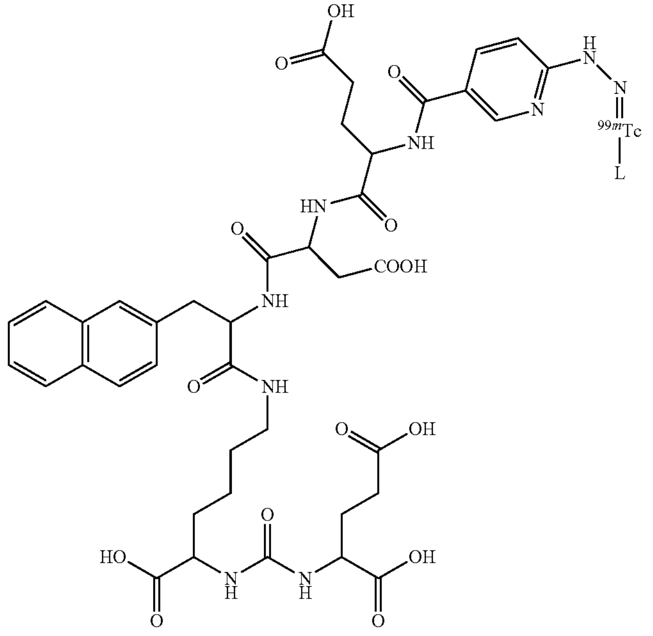
or -continued
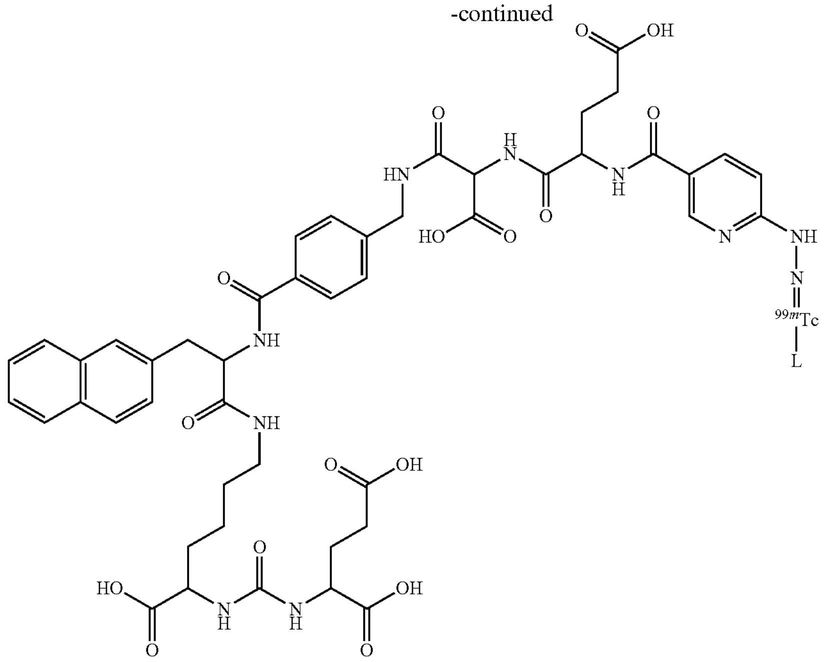
or
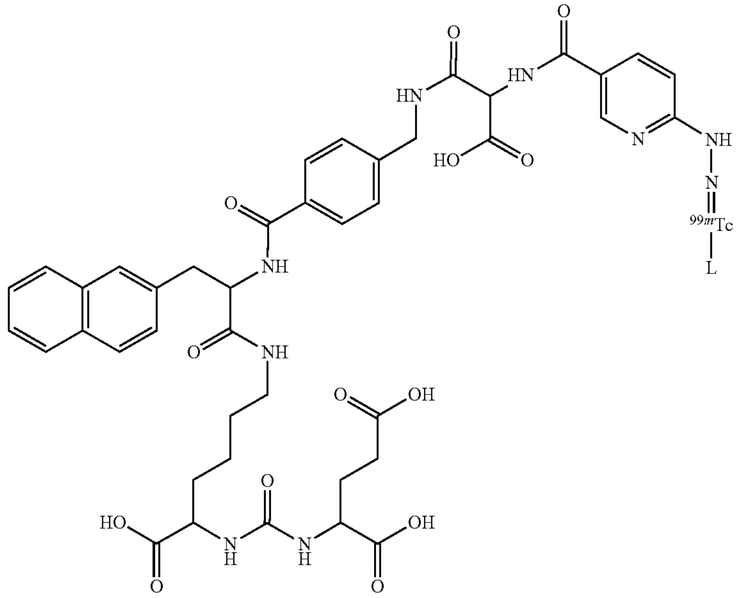
or
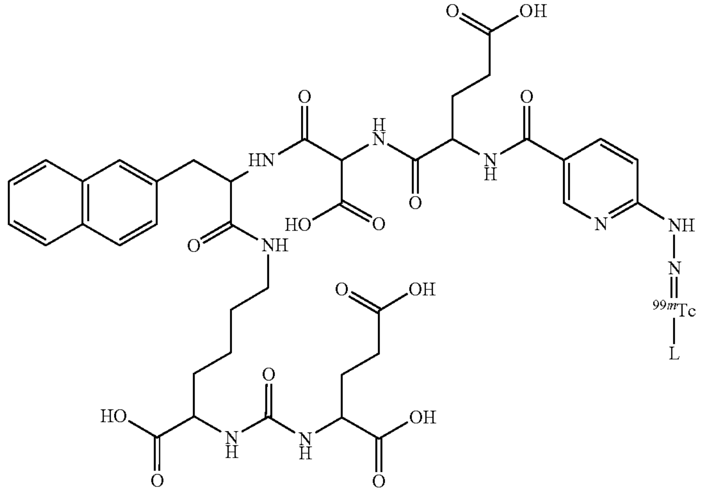
or -continued
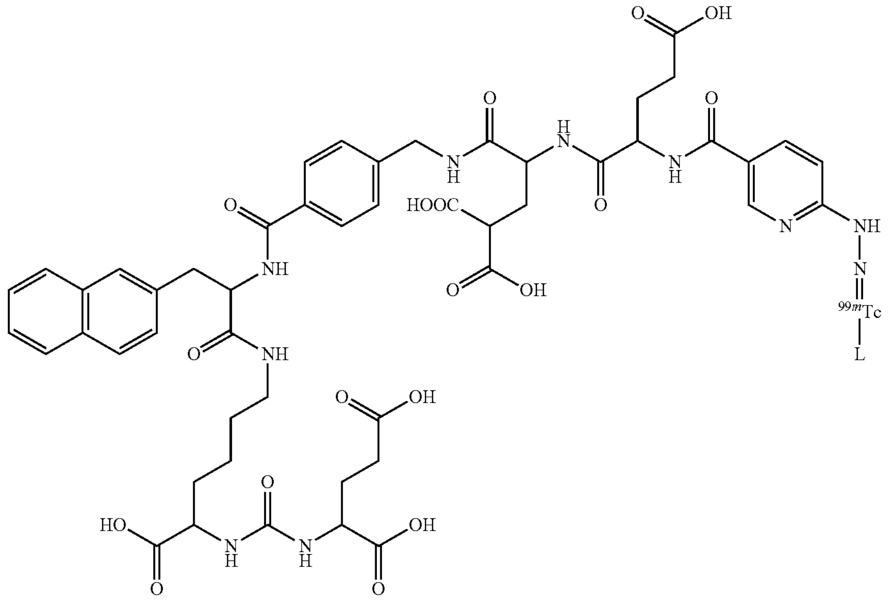
or
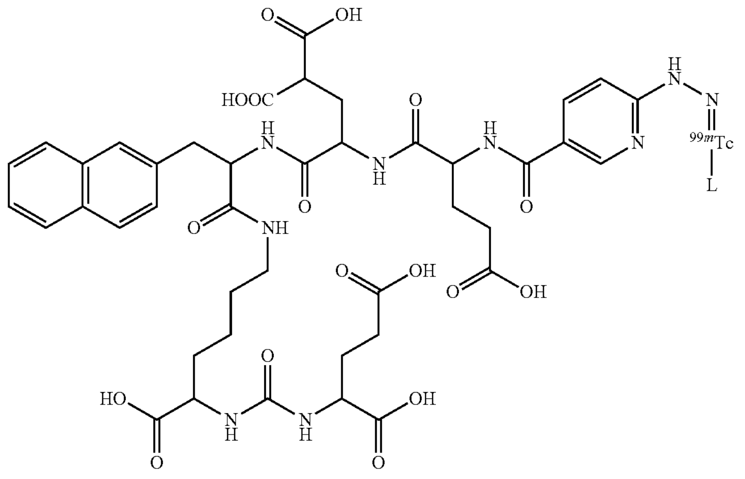
or
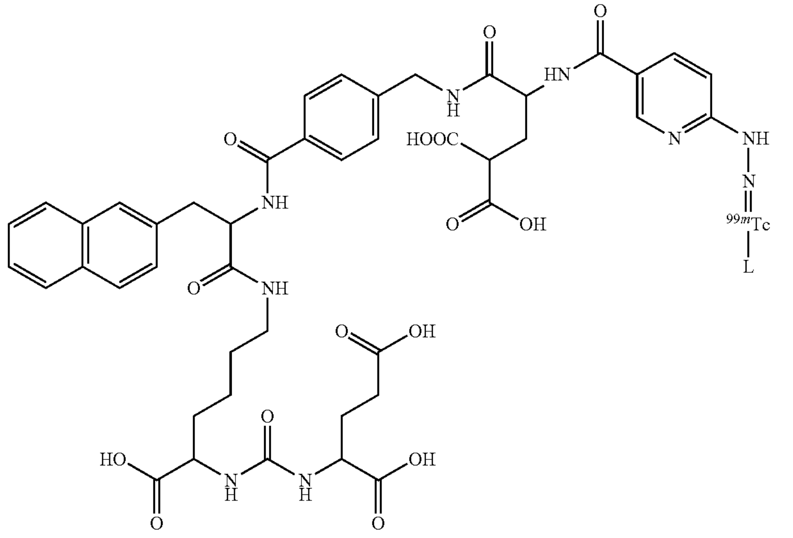
or -continued
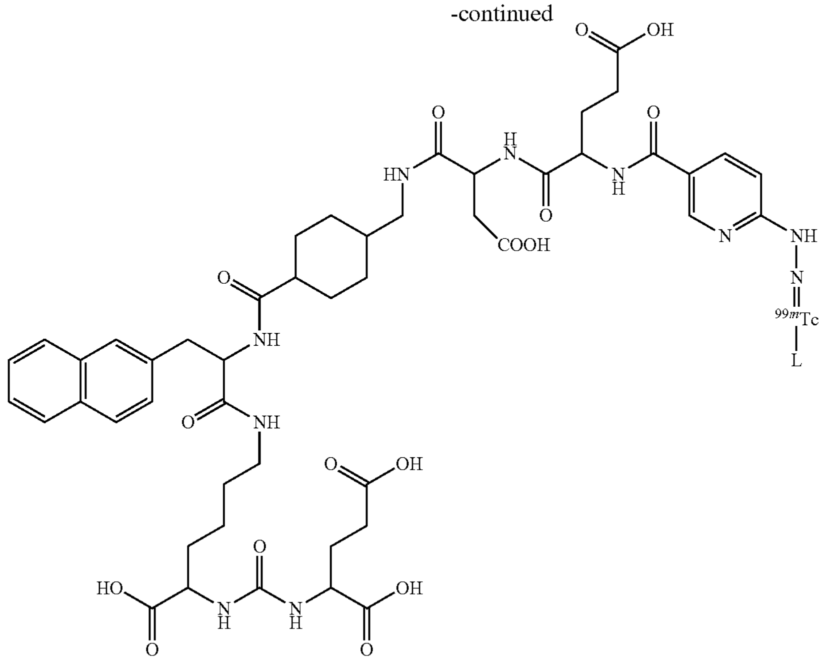
or
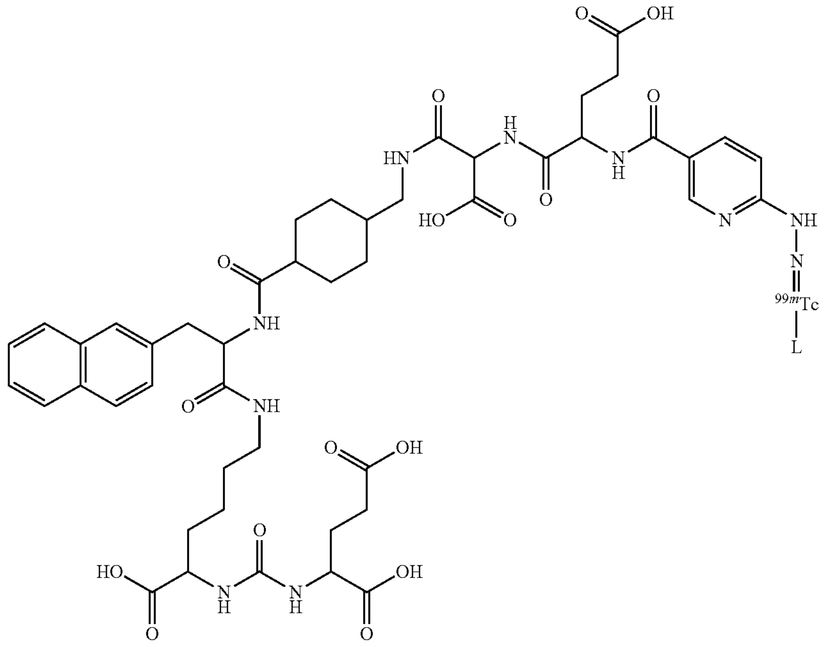
or -continued
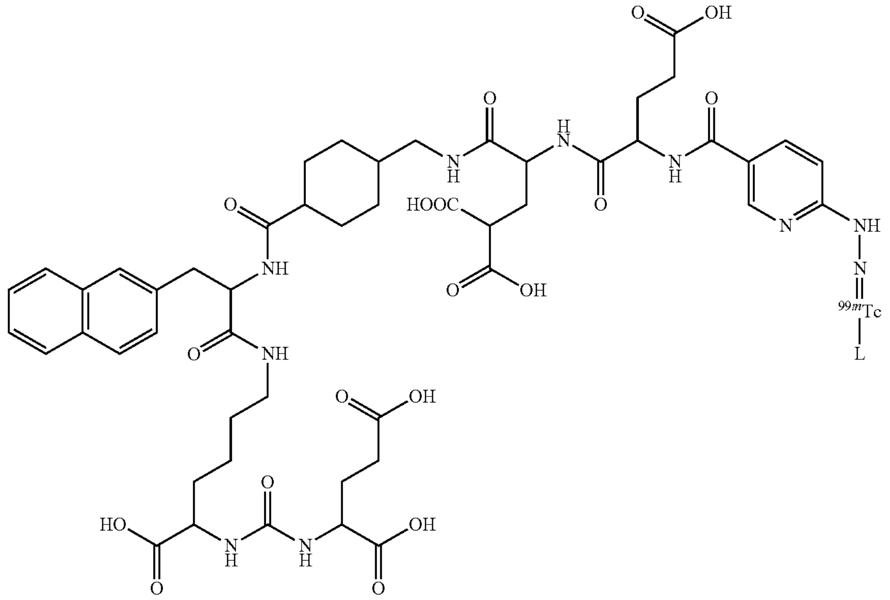
or
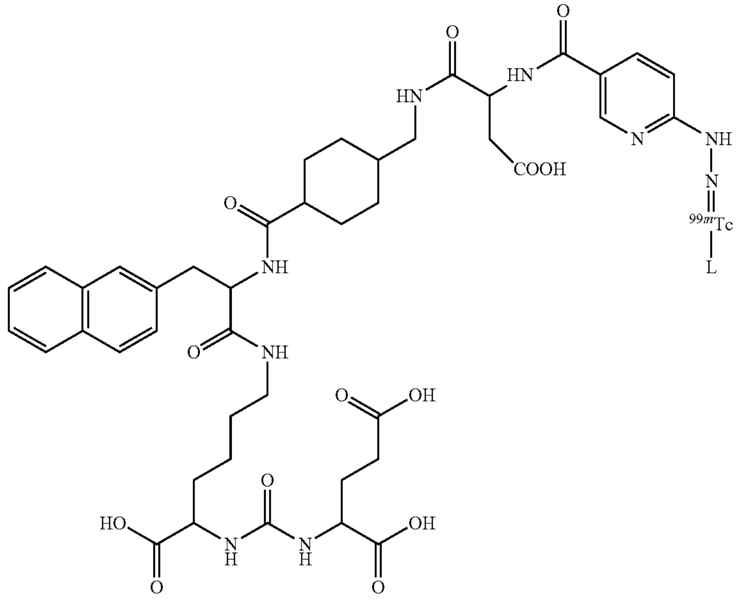
or -continued

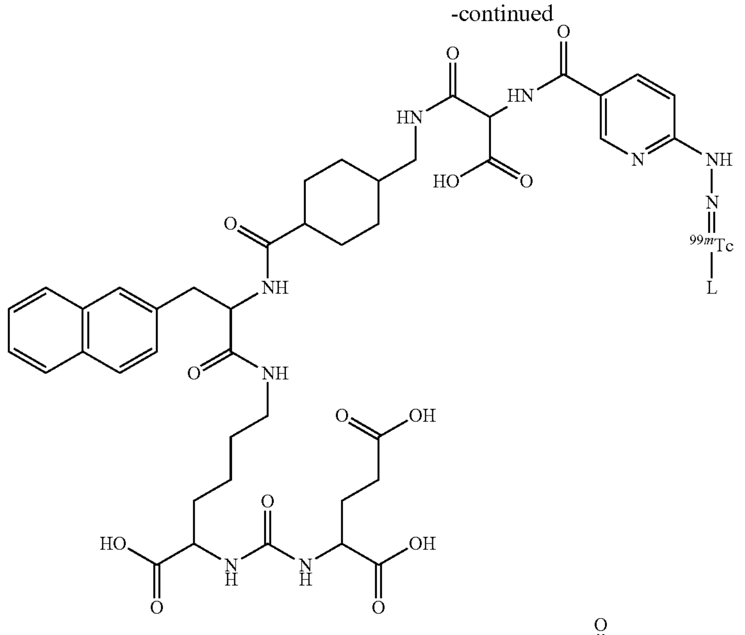

or

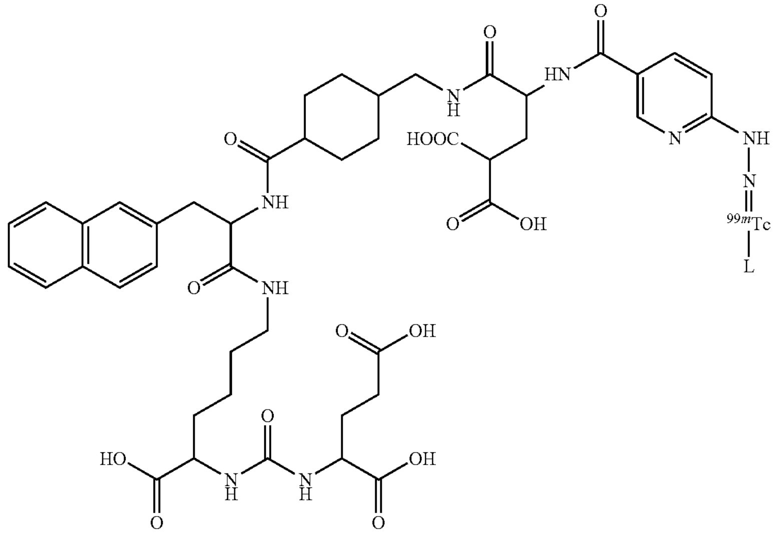

wherein:

L is N-tris(hydroxymethyl)methylglycine, ethylenediamine-N,N'-diacetic acid, triphenylphosphine-3,3',3''-trisulfonic acid trisodium, disodium 3,3'-(phenylphosphinediyl)bis(benzene-1-sulphonate), sodium diphenylphosphinobenzene-3-sulfonate, nicotinic acid, glucoheptonate, glucosamine, mannitol, or diphenylphosphinobenzoic acid.

The above compound or complex provided by the present invention can be used in a method for imaging in a patient, in a method for diagnosing prostate cancer and/or its metastases, or in a method for treating prostate cancer and/or its metastases.

The present invention further provides a pharmaceutical composition comprising the aforementioned compound or complex, or pharmaceutically acceptable prodrug, salt or ester thereof, and pharmaceutically acceptable carrier. The pharmaceutical composition can be used in a method for imaging in a patient, in a method for diagnosing prostate cancer and/or its metastases, or in a method for treating prostate cancer and/or its metastases.

The $^{99m}$Tc complex of general formula (II) of the present invention can be used for SPECT/CT imaging of prostate cancer and/or its metastases, and provides a new method for the diagnosis of prostate cancer. By modifying the intermediate linker of PSMA pharmacophoric group and radioactive coordination group, the lipophilicity of the compound is adjusted, the ratio of the compound metabolized by liver and gallbladder is increased, and the excretion of the compound from urinary system is reduced, therefore, the adverse effect of physiological uptake on imaging results is avoided. Compared to other existing PSMA SPECT tracers, the compounds of the present invention, especially $^{99m}$Tc-HYNIC-PSMA-XL-3, show excellent assessment of prostate cancer due to their low urinary clearance. Therefore, tracers in the present invention are suitable for the initial diagnosis of primary and recurrent prostate cancer.

DETAILED DESCRIPTION

The following embodiments describe the present invention in detail, and these embodiments are provided for illustration only, they should not to be construed in any way as limitation of the present invention.

Embodiment 1

Synthesis of Glu-Urea-Lys-2Nal-AMB-Glu-Glu-HYNIC (HYNIC-PSMA-XL-2)

It was synthesized by solid-phase synthesis using 2 mmol of tert-butyl ester-protected glutamic acid immobilized on 2-CTC resin as starting material, wherein 2 mol of N,N'-carbonyldiimidazole was added and then reacted at room temperature overnight. The unreacted N,N'-carbonyldiimidazole was eluted with DMF, methyl trifluoromethanesulfonate and triethylamine were added to react for 1 h, and then Fmoc-Lys(OtBu)-NH2 was added to react for 2 h. Then 1.96 mmol of HOBt and 2 mmol of DIC were used as amidation catalysts in DMF, followed by adding 2 mmol of Fmoc-2Nal-OH, Fmoc-4-aminomethyl-benzoic acid, Fmoc-Glu(OtBu)-OH, Fmoc-Glu(OtBu)-OH and Boc-HYNIC successively. Finally, the 2-CTC resin and the tert-butyl ester were removed with a mixture consisting of trifluoroacetic acid, triisopropylsilane and water (95/2.5/2.5) to obtain a crude product.

Figure 1:
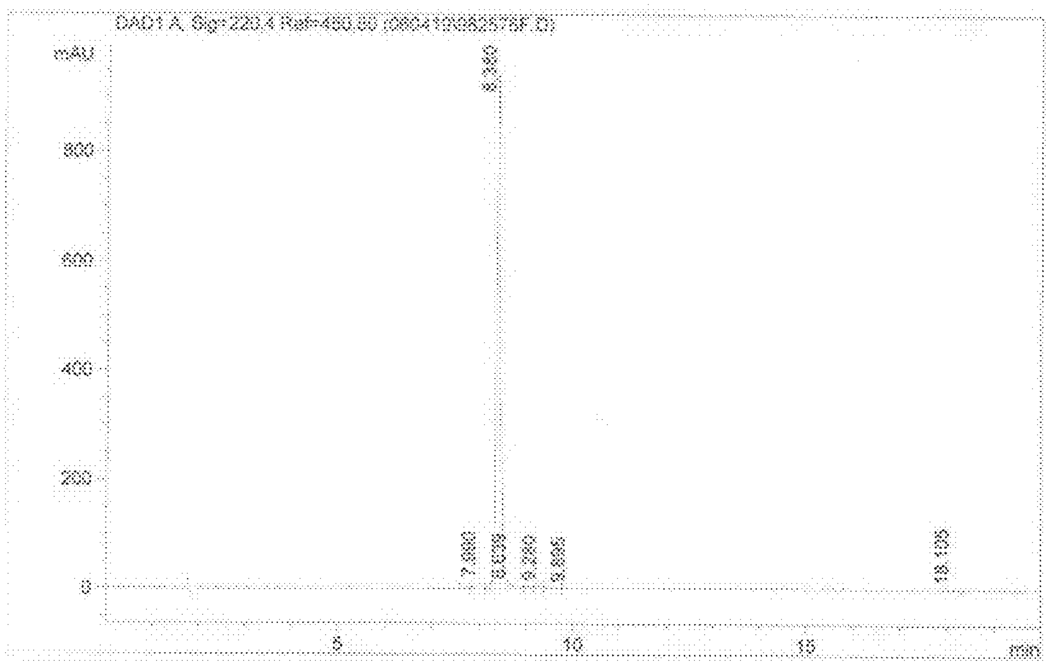
FIG. 1 shows an HPLC UV-vis spectrum of HYNIC-PSMA-XL-2.
Figure 2:
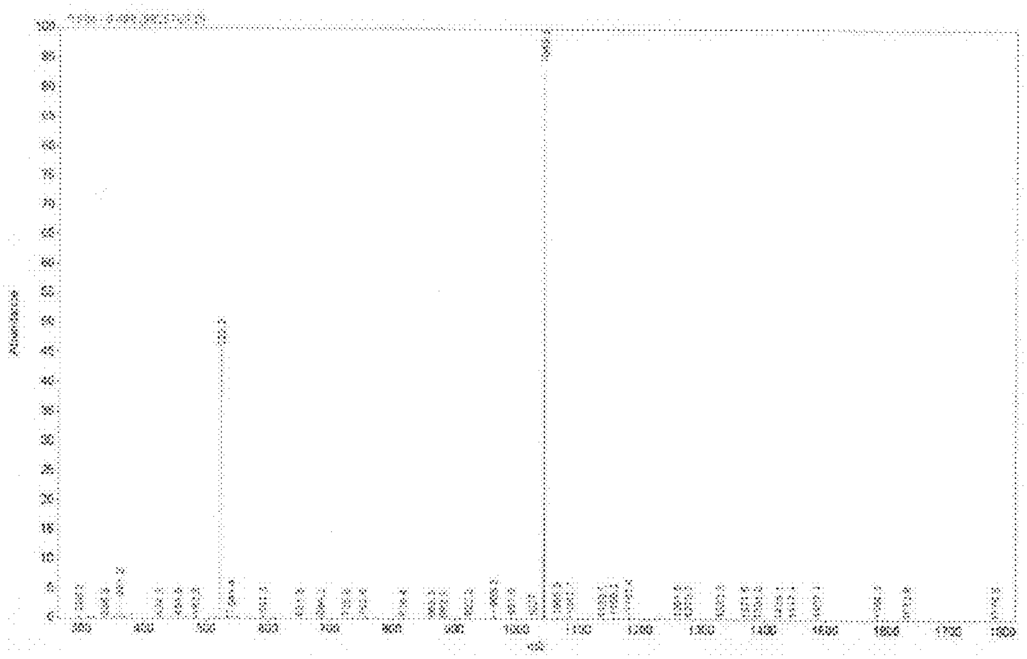
FIG. 2 shows a mass spectrum of HYNIC-PSMA-XL-2.

The obtained crude product was separated and purified by preparative RP-HPLC, and then the purified product was analyzed by analytical RP-HPLC and LC-MS. The HPLC spectrum was shown in FIG. 1, and the mass spectrum was shown in FIG. 2.

Synthetic reaction scheme of HYNIC-PSMA-XL-2
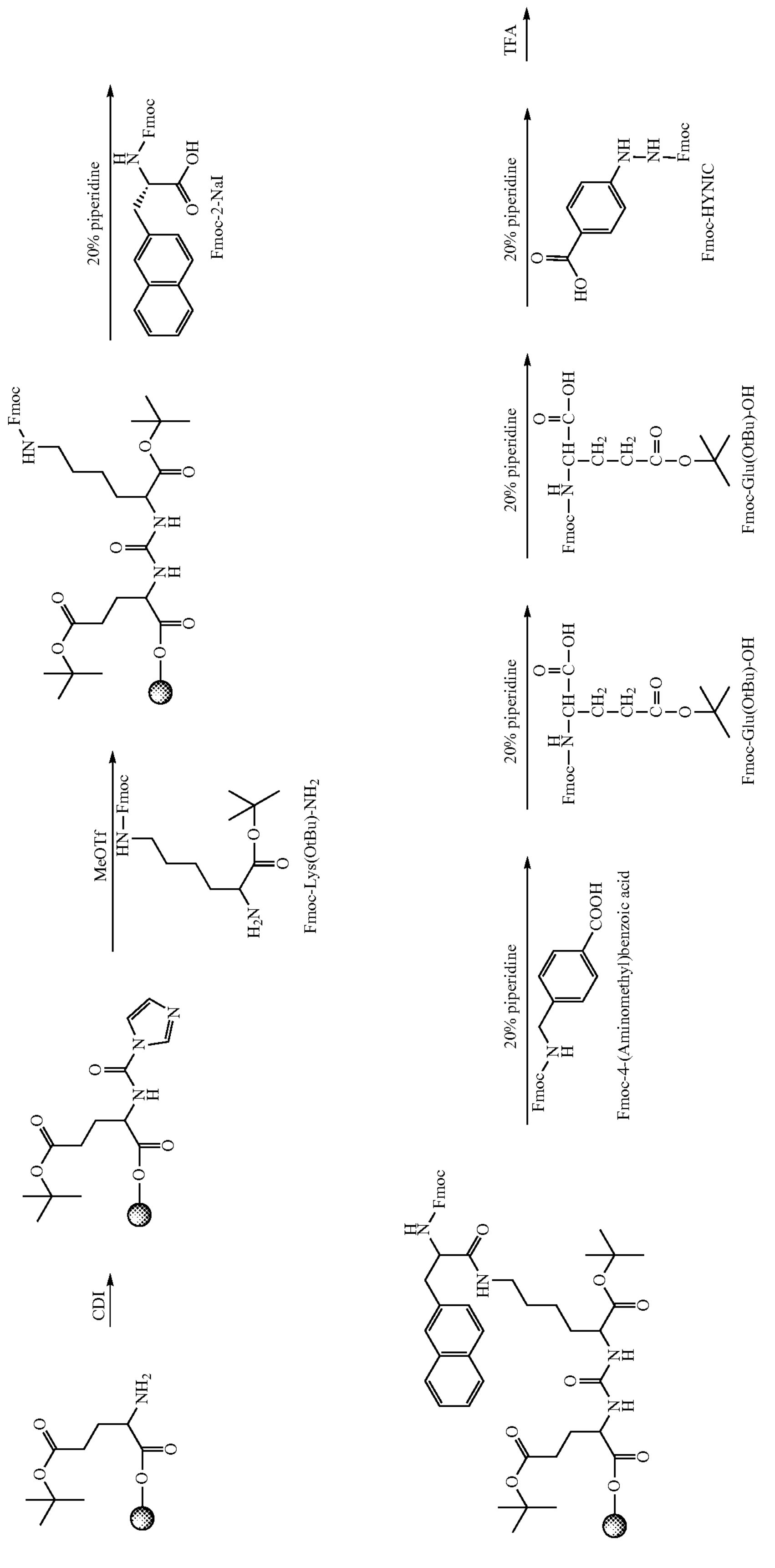

-continued
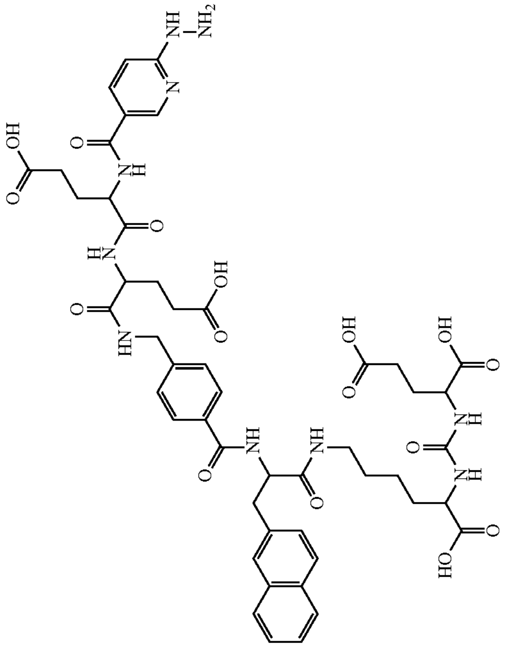
HYNIC-PSMA-XL-2
2-CTC

Embodiment 2

Synthesis of Glu-Urea-Lys-2Nal-AMB-Glu-HYNIC (HYNIC-PSMA-XL-3)

It was synthesized by solid-phase synthesis using 2 mmol of tert-butyl ester-protected glutamic acid immobilized on 2-CTC resin as starting material, wherein 2 mol of N,N'-carbonyldiimidazole was added and then reacted at room temperature overnight. The unreacted N,N'-carbonyldiimidazole was eluted with DMF, methyl trifluoromethanesulfonate and triethylamine were added to react for 1 h, and then Fmoc-Lys(OtBu)-NH2 was added to react for 2 h. After that, 1.96 mmol of HOBt and 2 mmol of DIC were used as amidation catalysts in DMF, followed by adding 2 mmol of Fmoc-2Nal-OH, Fmoc-4-aminomethyl-benzoic acid, Fmoc-Glu(OtBu)-OH and Boc-HYNIC successively. Finally, the 2-CTC resin and the tert-butyl ester were removed with a mixture consisting of trifluoroacetic acid, triisopropylsilane and water (95/2.5/2.5) to obtain a crude product.

Figure 3:
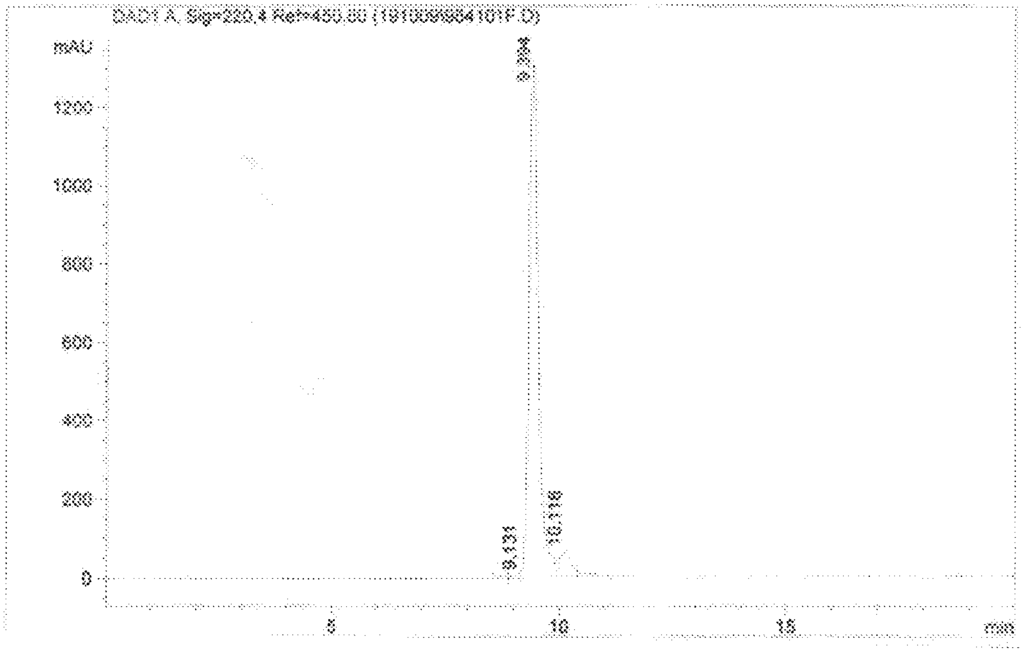
FIG. 3 shows an HPLC UV spectrum of HYNIC-PSMA-XL-3.
Figure 4:
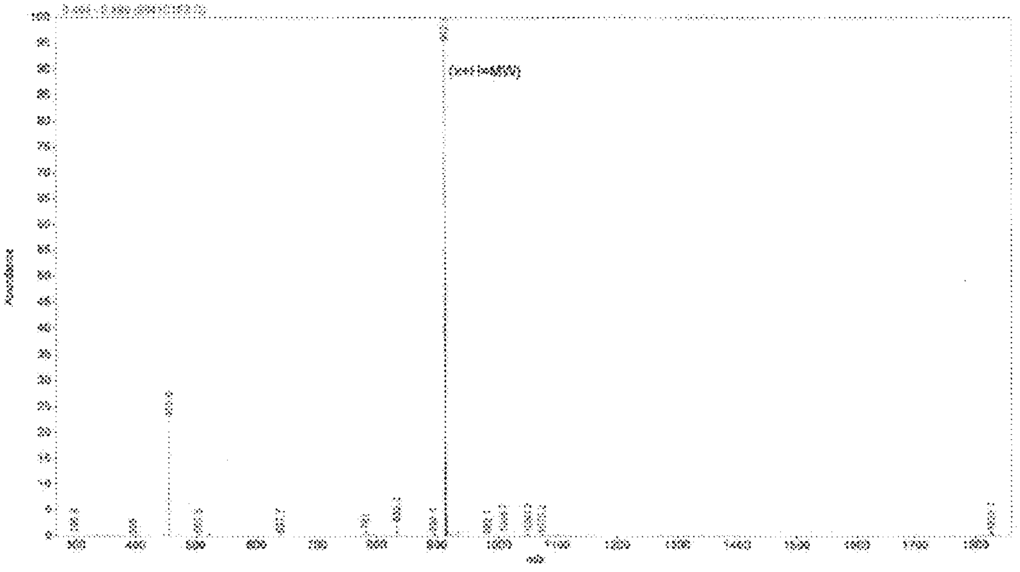
FIG. 4 shows a mass spectrum of HYNIC-PSMA-XL-3.

The obtained crude product was separated and purified by preparative RP-HPLC, and then the purified product was analyzed by analytical RP-HPLC and LC-MS. The HPLC spectrum was shown in FIG. 3, and the mass spectrum was shown in FIG. 4.

Synthetic reaction scheme of HYNIC-PSMA-XL-3
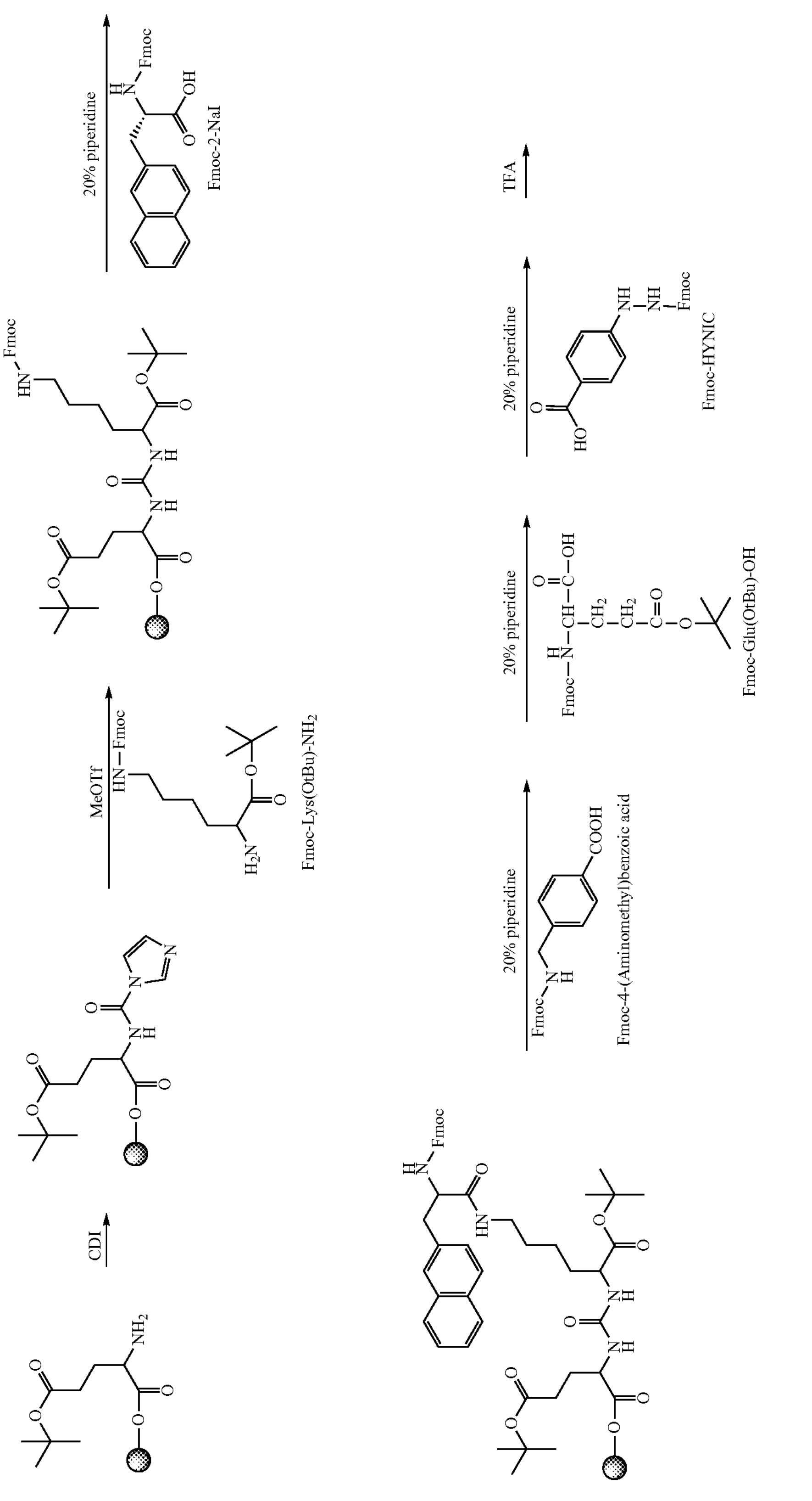

-continued
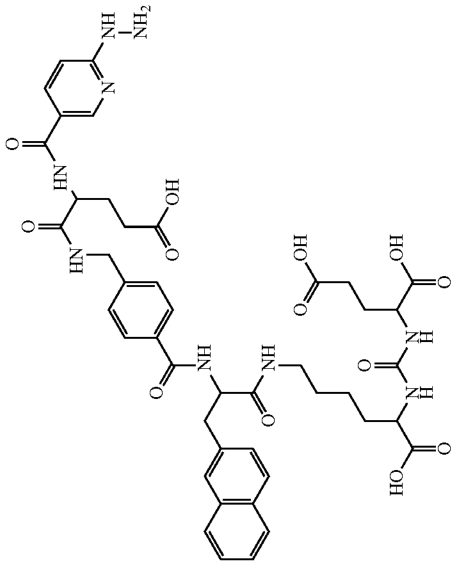
HYNIC-PSMA-XL-3
2-CTC

Embodiment 3

HYNIC-PSMA-XL-2 and HYNIC-PSMA-XL-3 Affinity Assay

The binding capacity of HYNIC-PSMA-XL-2 and HYNIC-PSMA-XL-3 to PSMA protein was determined by Surface Plasmon Resonance (SPR). Since the dissociations of HYNIC-PSMA-XL-2 and HYNIC-PSMA-XL-3 were both very slow with a kd beyond the detection limit of the instrument (1E-6), the final calculated KD of the binding of HYNIC-PSMA-XL-2 and PSMA protein should be less than 6.43 pM, and the calculated KD of the binding of HYNIC-PSMA-XL-3 and PSMA protein should be less than 4.857 pM based on the ka results. In order to compare with the reported PSMA inhibitors, the binding capacity of PSMA11, $^{19}$F-PSMA1007, 2-PMPA and HYNIC-ALUG compounds publicly reported by our research group were determined by the same method. The specific KD values are listed in Table 1.

TABLE 1

Affinity KD values of different PSMA inhibitors to PSMA

| Compound | KD value (SPR method) |
|---|---|
| HYNIC-PSMA-XL-2 | <6.43 pM |
| HYNIC-PSMA-XL-3 | <4.897 pM |
| 2-PMPA | 9.868 nM |

TABLE 1-continued

Affinity KD values of different PSMA inhibitors to PSMA

| Compound | KD value (SPR method) |
|---|---|
| PSMA11 | 1.255 nM |
| $^{19}$F-PSMA1007 | 64.92 nM |
| HYNIC-ALUG | 299.4 nM |

Embodiment 4

Figure 5:
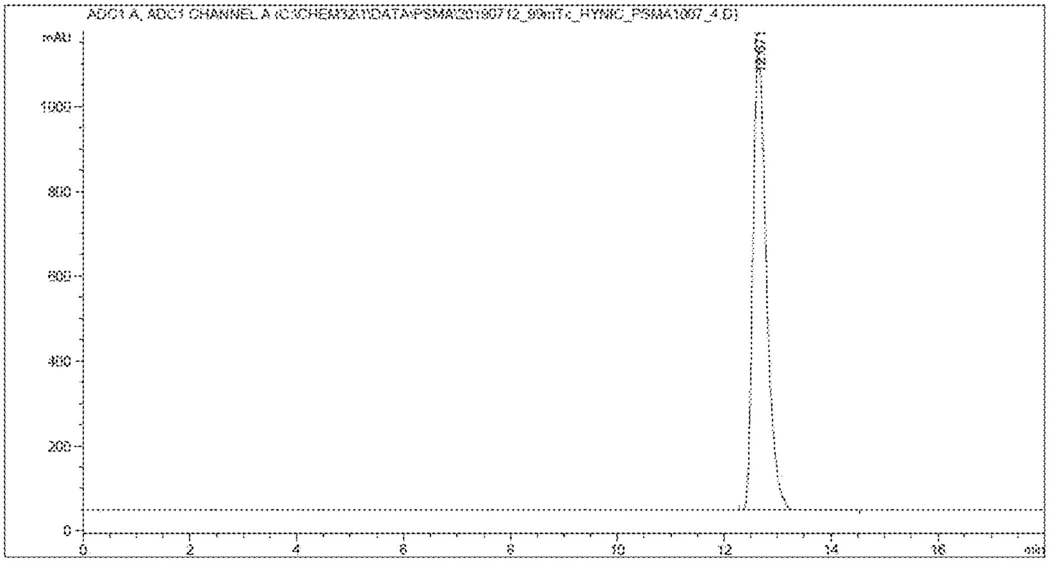
FIG. 5 shows a Radio-HPLC spectrum of $^{99m}$Tc-HYNIC/EDDA-PSMA-XL-2.

Preparation of $^{99m}$Tc-HYNIC/EDDA-PSMA-XL-2 Complex:

1 μg of HYNIC-PSMA-XL-2, 5 mg of ethylenediamine-N,N'-diacetic acid, 50 mg of disodium succinate, 30 mg of succinic acid, 20 mg of Tricine, 100 mg of mannitol and 30 μg of stannous chloride were dissolved in 1 ml of sterile water for injection, then 0.5 ml of Na$^{99m}$TcO$_4$ eluent (1100 MBq) was added, after that the mixture was reacted in a boiling water bath for 20 min to obtain the target compound $^{99m}$Tc-HYNIC/EDDA-PSMA-XL-2. The target compound has a radiochemical purity greater than 99% determined by Radio-HPLC. The relevant analytical spectrum was shown in FIG. 5.

Synthetic reaction scheme of $^{99m}$Tc-HYNIC/EDDA-PSMA-XL-2

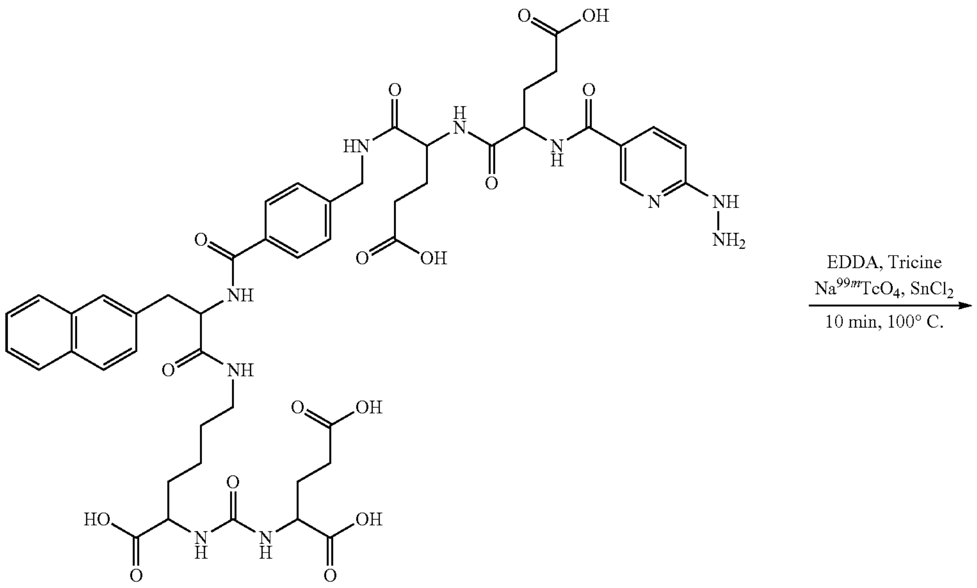

HYNIC-PSMA-XL-2

-continued

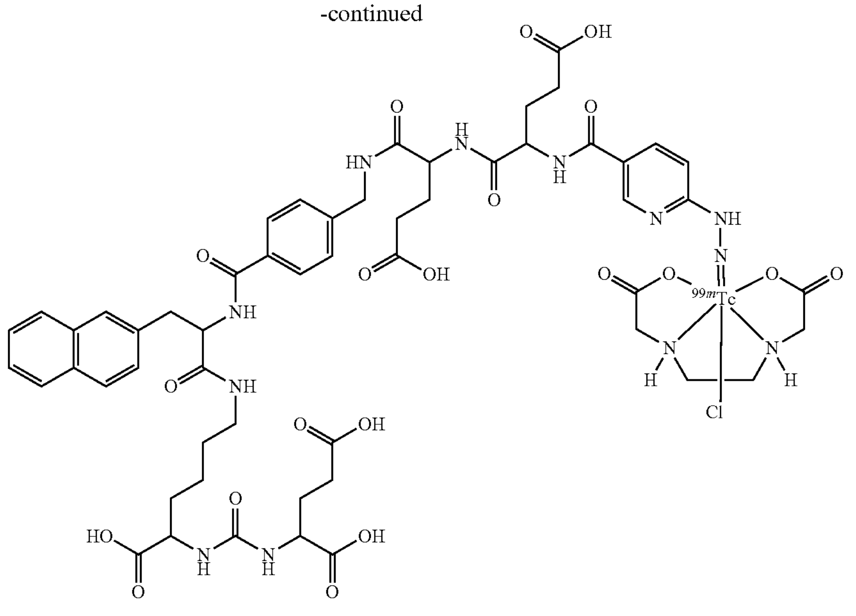

$^{99m}$Tc-HYNIC/EDDA-PSMA-XL-2

Embodiment 5

Figure 6:
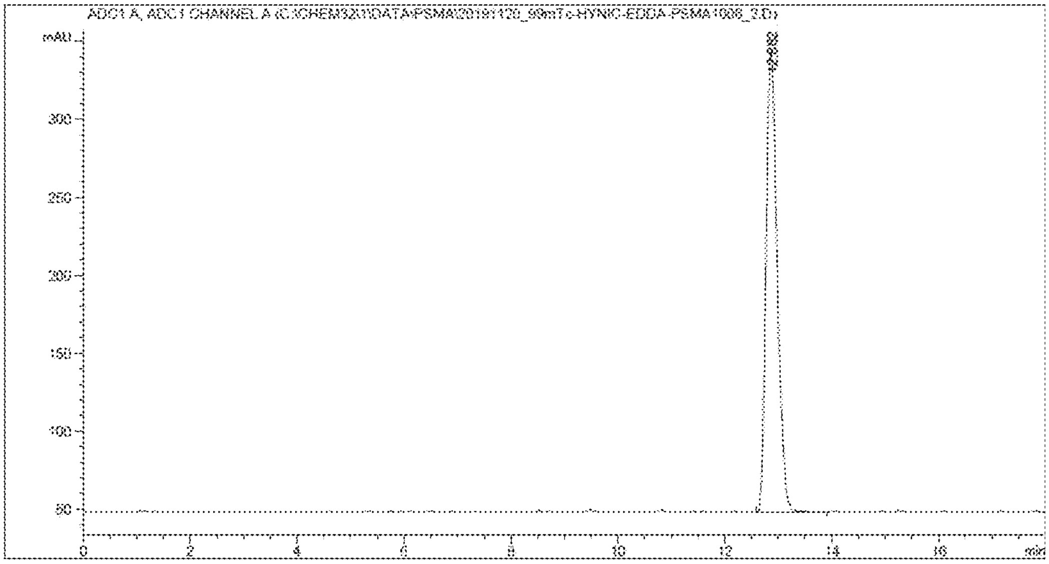
FIG. 6 shows a Radio-HPLC spectrum of $^{99m}$Tc-HYNIC/EDDA-PSMA-XL-3.

Preparation of $^{99m}$Tc-HYNIC/EDDA-PSMA-XL-3 Complex:

10 μg of HYNIC-PSMA-XL-3, 50 mg of ethylenediamine-N,N'-diacetic acid, 20 mg of disodium succinate, 10 mg of succinic acid, 1 mg of Tricine, 40 mg of mannitol and 500 μg of stannous chloride were dissolved in 0.5 ml of sterile water for injection, then 2 ml of $Na^{99m}TcO_4$ eluent (1100 MBq) was added, after that the mixture was reacted in a boiling water bath for 20 min to obtain the target compound $^{99m}$Tc-HYNIC/EDDA-PSMA-XL-3. The target compound has a radiochemical purity greater than 99% determined by Radio-HPLC. The relevant analytical spectrum was shown in FIG. 6.

Synthetic reaction scheme of $^{99m}$Tc-HYNIC/EDDA-PSMA-XL-3

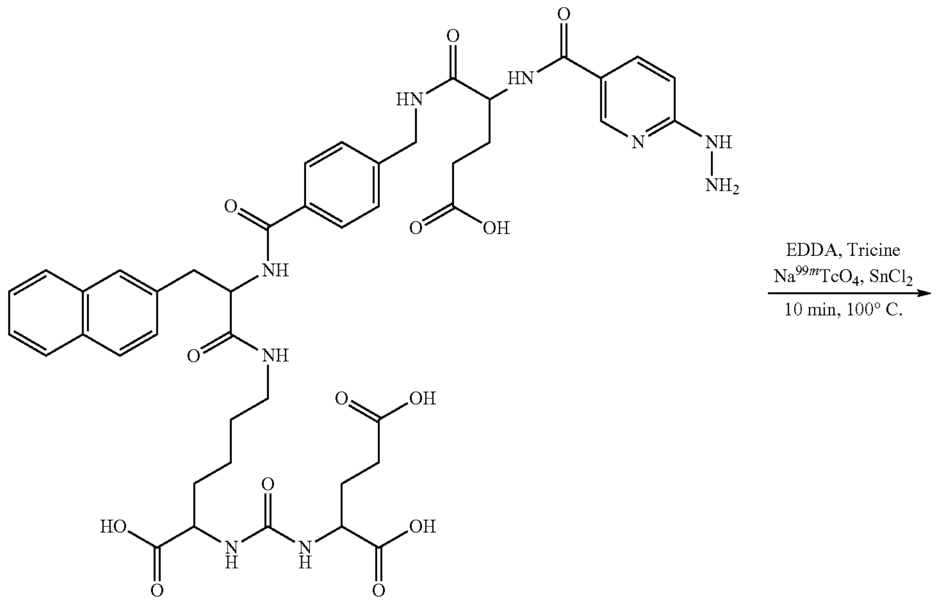

HYNIC-PSMA-XL-3

-continued

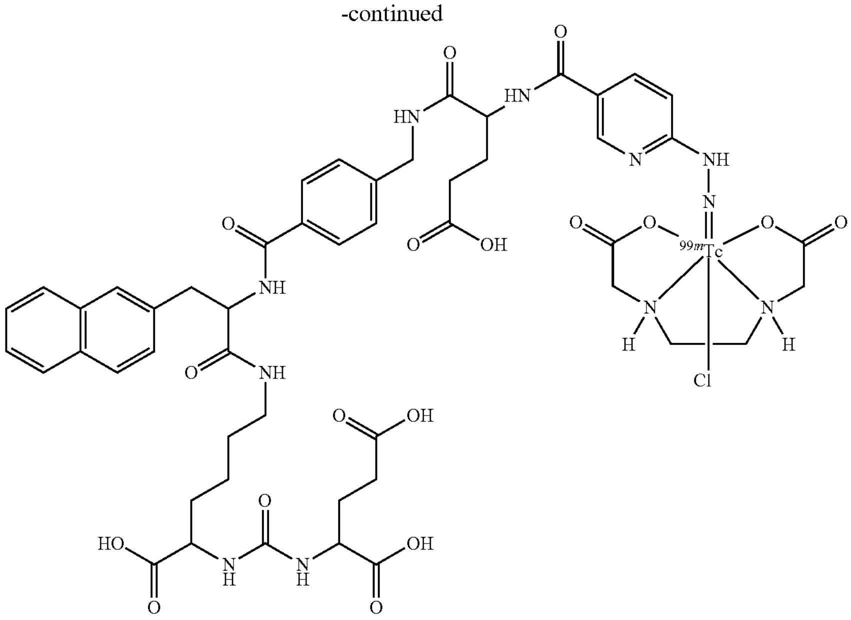

$^{99m}$Tc-HYNIC/EDDA-PSMA-XL-3

Embodiment 6

Preparation of $^{99m}$Tc-HYNIC/TPPTS-PSMA-XL-2 Complex

Figure 7:
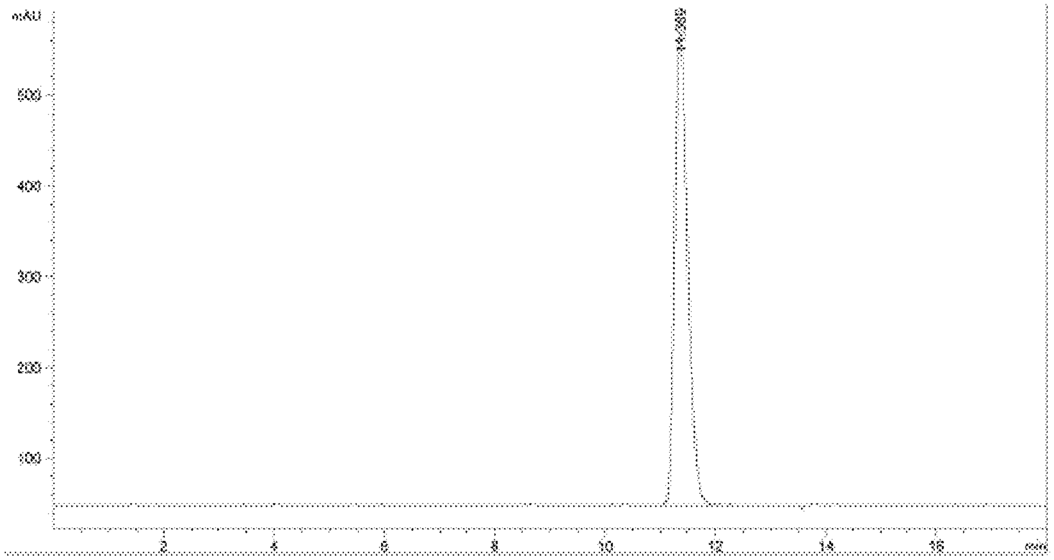
FIG. 7 shows a Radio-HPLC spectrum of $^{99m}$Tc-HYNIC/TPPTS-PSMA-XL-2.

50 μg of HYNIC-PSMA-XL-2, 1 mg of triphenylphosphine-3,3',3"-trisulfonic acid trisodium, 35 mg of disodium succinate, 5 mg of succinic acid, 15 mg of Tricine and 10 μg of stannous chloride were dissolved in 0.8 ml of sterile water for injection, then 1 ml of Na$^{99m}$TcO$_4$ eluent (1100 MBq) was added, after that the mixture was reacted in a boiling water bath for 20 min to obtain the target compound $^{99m}$Tc-HYNIC/TPPMS-PSMA-XL-2. The target compound has a radiochemical purity greater than 99% determined by Radio-HPLC. The relevant analytical spectrum was shown in FIG. 7.

Synthetic reaction scheme of $^{99m}$Tc-HYNIC/TPPTS-PSMA-XL-2

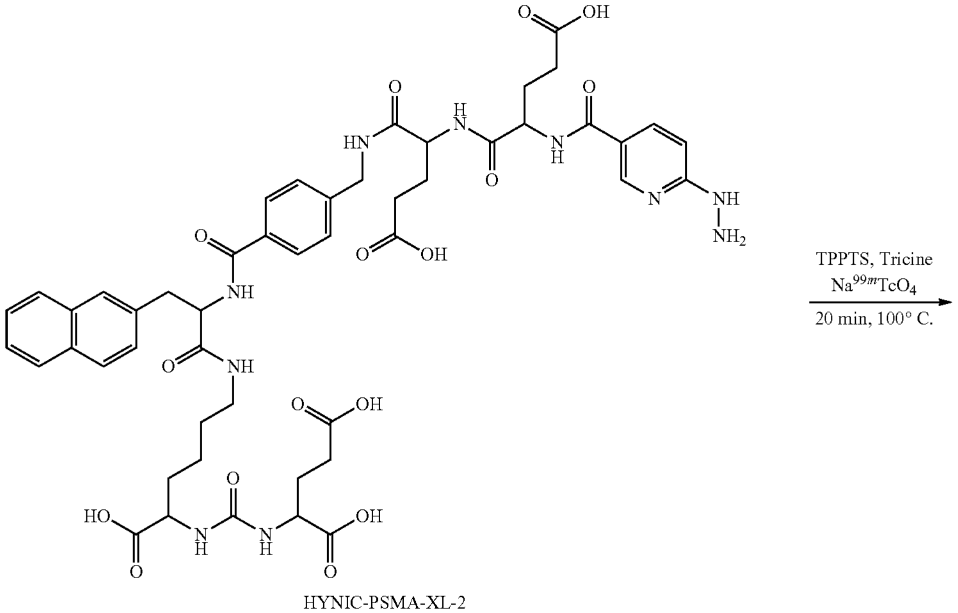

HYNIC-PSMA-XL-2

-continued

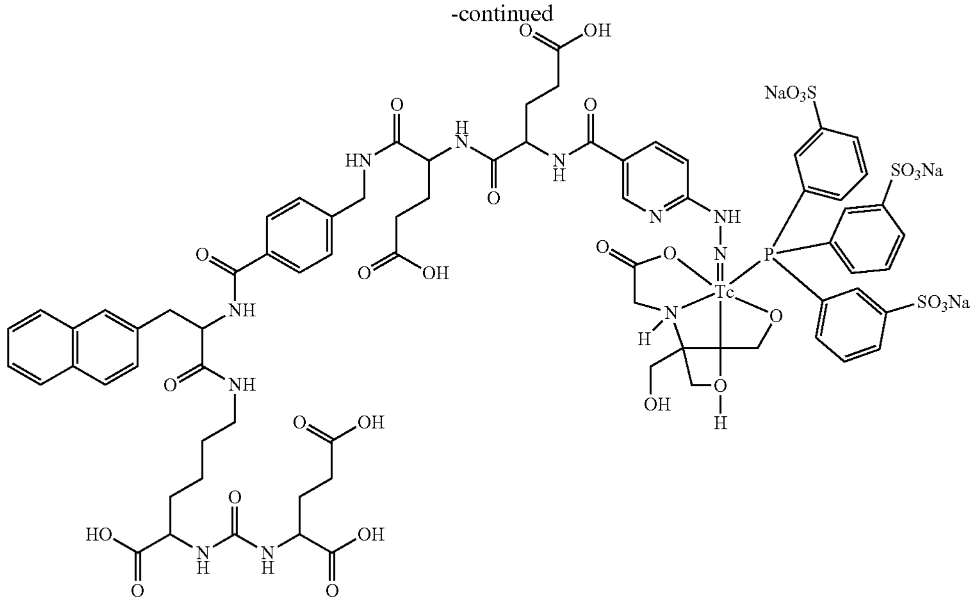

$^{99m}$Tc-HYNIC/TPPTS-PSMA-XL-2

Embodiment 7

Preparation of the $^{99m}$Tc-HYNIC/TPPTS-PSMA-XL-3 Complex

Figure 8:
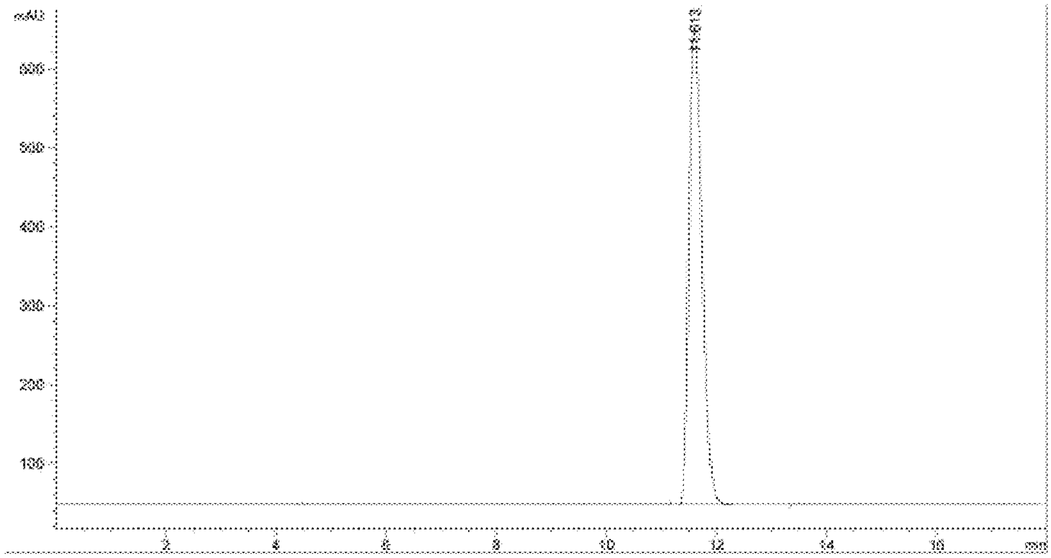
FIG. 8 shows a Radio-HPLC spectrum of $^{99m}$Tc-HYNIC/TPPTS-PSMA-XL-3.

100 μg of HYNIC-PSMA-XL-3, 25 mg of Triphenylphosphine-3,3',3"-trisulfonic acid trisodium, 45 mg of disodium succinate, 20 mg of succinic acid, 50 mg of Tricine and 60 mg of mannitol were dissolved in 2 ml of sterile water for injection, then 1 ml of Na$^{99m}$TcO$_4$ eluent (1100 MBq) was added, after that the mixture was reacted in a boiling water bath for 20 min to obtain the target compound $^{99m}$Tc-HYNIC/TPPMS-PSMA-XL-3. The target compound has a radiochemical purity greater than 99% determined by Radio-HPLC. The relevant analytical spectrum was shown in FIG. 8.

Synthetic reaction scheme of $^{99m}$Tc-HYNIC/TPPTS-PSMA-XL-3

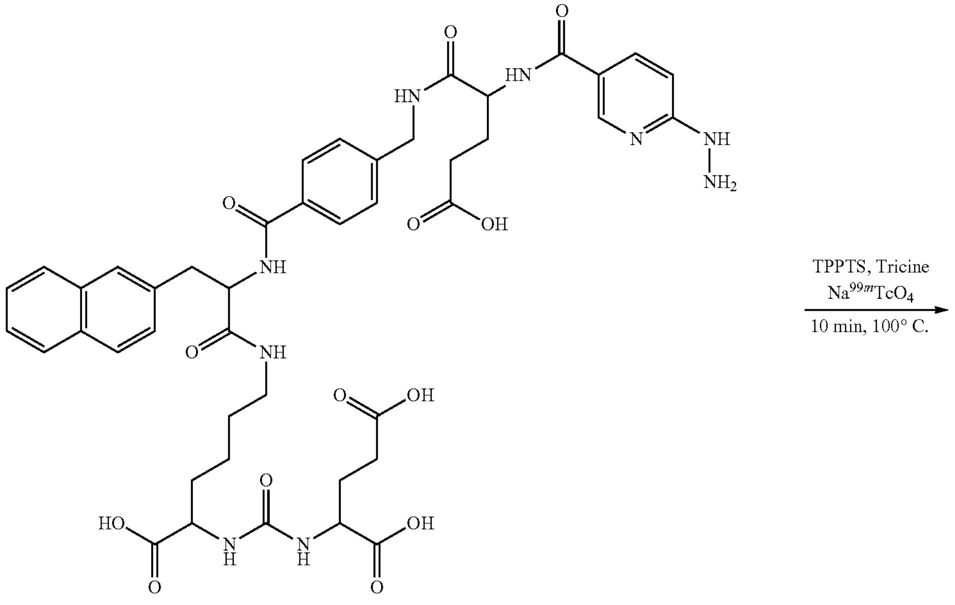

HYNIC-PSMA-XL-3

-continued

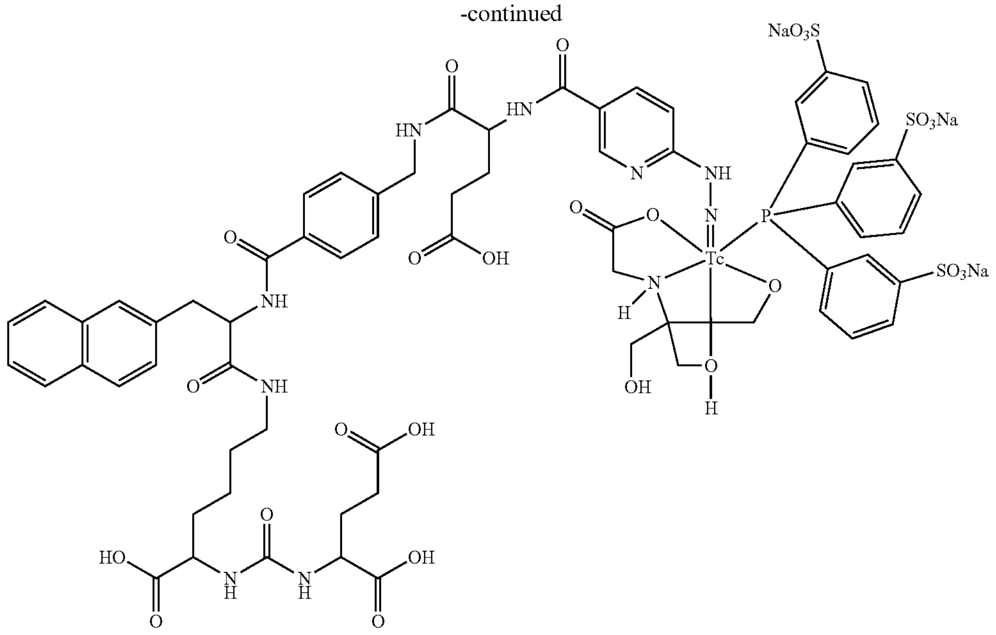

${}^{99m}$Tc-HYNIC/TPPTS-PSMA-XL-3

Embodiment 8

Figure 9:
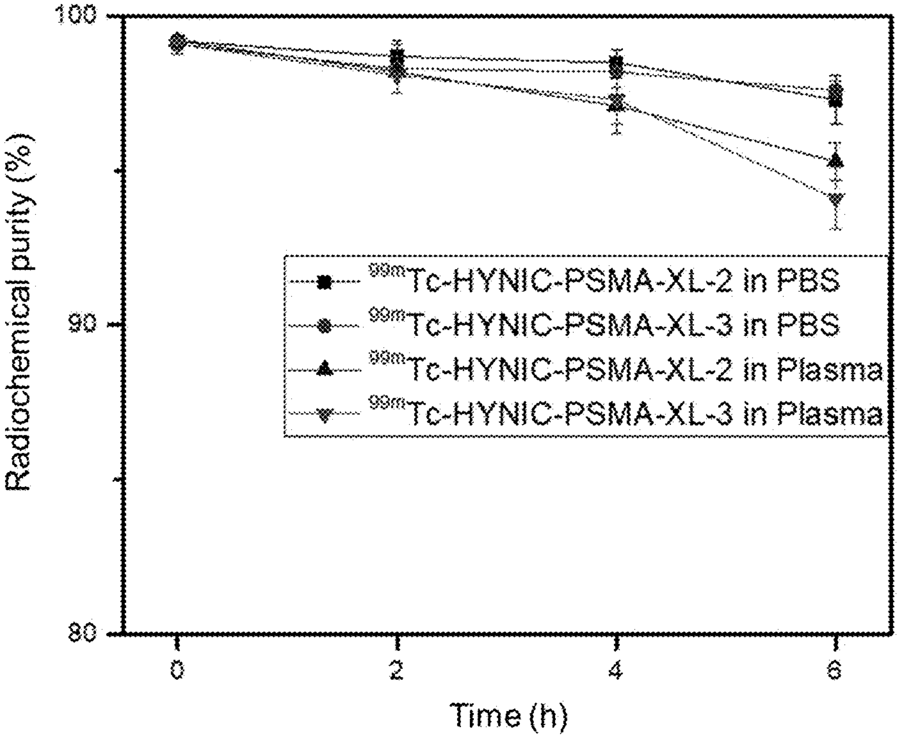
FIG. 9 shows the stability of $^{99m}$Tc-HYNIC/EDDA-PSMA-XL-2 and $^{99m}$Tc-HYNIC/EDDA-PSMA-XL-3 in vitro.

In Vitro Stability Experiments of the Complexes:

A certain amount of ${}^{99m}$Tc-HYNIC/EDDA-PSMA-XL-2 and ${}^{99m}$Tc-HYNIC/EDDA-PSMA-XL-3 were added to PBS and fresh mouse serum respectively, and the radiochemical purity was determined at different time points to detect the stability of the two complexes. The results were shown in FIG. 9, the two complexes both have radiochemical purity greater than 90% and maintain high stability after 6 h.

Embodiment 9

Cell Uptake Experiments:

Human prostate cancer LNCaP cells (PSMA positive) were cultured in a RPMI 1640 medium containing 10% fetal bovine serum and 1% penicillin-streptomycin double antibody under 37° C. with 5% $CO_2$ and saturated humidity in the incubator. When the cells reach log phase, they were digested with 0.25% trypsin, then the cells were collected and washed twice with PBS, after that a cell suspension was obtained for further culture. A fixed number of cell lines ($1.0\times10^6$ cells/1 ml) was placed in each well of a 24-well cell culture dish, and the experiment was performed after the logarithmic growth phase.

The cells were divided into an experimental group and a blocking group. 0.5 μCi of the complex ${}^{99m}$Tc-HYNIC/EDDA-PSMA-XL-2 or ${}^{99m}$Tc-HYNIC/EDDA-PSMA-XL-3 was added to each well, wherein an excess of PSMA inhibitor 2-PMPA (1000-fold molar equivalent) was added to the blocking group half an hour in advance. 6 groups of experiments were carried out in parallel. After 1 h, the culture medium was aspirated, placed in a γ-counting tube, and then washed three times with PBS. The washing solution and the culture medium were combined for storage. Then the cells were trypsinized, collected in another counting tube, and the percentage of cell uptake was calculated by a γ-counting tube. The results were shown in Table 2:

TABLE 2

Results of LNCaP cell uptake experiments

| Compound | Experimental group | Blocking group |
|---|---|---|
| HYNIX-PSMA-XL-2 | 16.54 ± 1.33% | 3.07 ± 0.80% |
| HYNIX-PSMA-XL-3 | 14.01 ± 1.11% | 2.66 ± 0.51% |

The results show that both ${}^{99m}$Tc-HYNIX-PSMA-XL-2 and ${}^{99m}$Tc-HYNIX-PSMA-XL-3 could highly specifically bind to PSMA-positive LNCaP cells.

Embodiment 10

SPECT Imaging Studies:

Male SCID mice weighing 18-20 g, were provided by SHANGHAI SLAC LABORATORY ANIMAL CO. LTD, and were raised in the SPF class animal laboratory of the Laboratory Animal Department of Fudan University. After two days of adaptive feeding in the animal room, LNCaP human prostate cancer cells were injected subcutaneously into the armpit of nude mice with an injection volume of 0.2 ml ($1\times10^7$ cells/ml dispersed in 50% Matrigel). The feeding was continued for 4-6 weeks after injection, and the mice were used for imaging experiments when their solid tumor mass grows to 500-600 $mm^3$.

Figure 10:
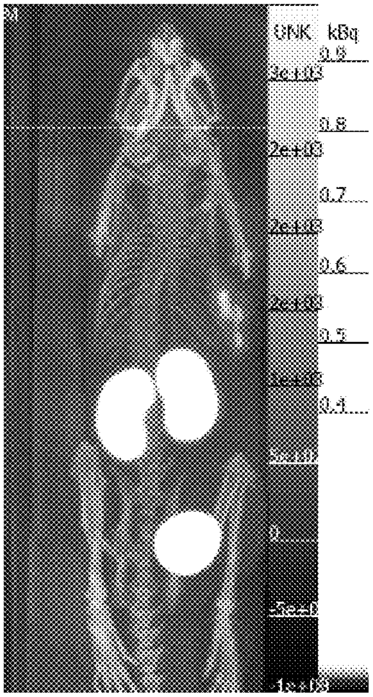
FIG. 10 shows an SPECT/CT image of $^{99m}$Tc-HYNIC/EDDA-PSMA-XL-2 imaging under a LNCaP tumor model.
Figure 11:
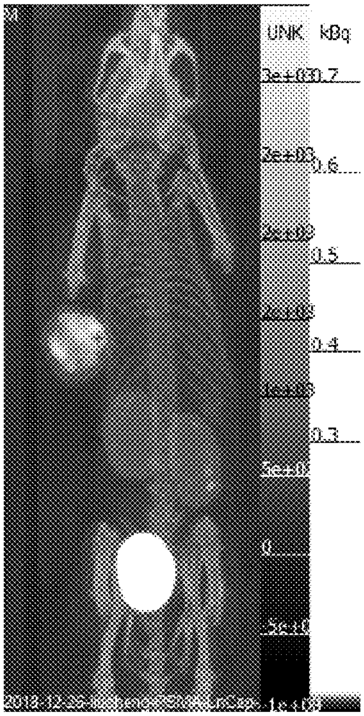
FIG. 11 shows an SPECT/CT image of $^{99m}$Tc-HYNIC/EDDA-PSMA-XL-3 imaging under the LNCaP tumor model.

1 mCi/0.2 ml of the ${}^{99m}$Tc-HYNIC/EDDA-PSMA-XL-2 or ${}^{99m}$Tc-HYNIC/EDDA-PSMA-XL-3 complex was injected into tail vein of the tumor-bearing mice. 2 hours after injection, the experimental animals were imaged with Small-Animal SPECT/CT. The images were shown in FIGS. 10 and 11.

Male Balb/c nude mice weighing 18-20 g, were provided by SHANGHAI SLAC LABORATORY ANIMAL CO. LTD, and were raised in the SPF class animal laboratory of the Laboratory Animal Department of Fudan University. After two days of adaptive feeding in the animal room, PC-3 human prostate cancer cells were injected subcutaneously into the armpit of nude mice with an injection volume of 0.2 ml. The feeding was continued for 4-6 weeks after injection, and the mice were used for imaging experiments when the solid tumor mass grows to 500-600 $mm^3$.

Figure 12:
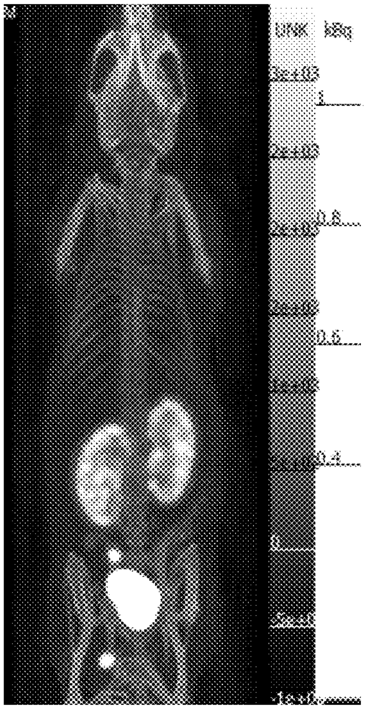
FIG. 12 shows an SPECT/CT image of $^{99m}$Tc-HYNIC/EDDA-PSMA-XL-2 imaging under a PC-3 tumor model.
Figure 13:
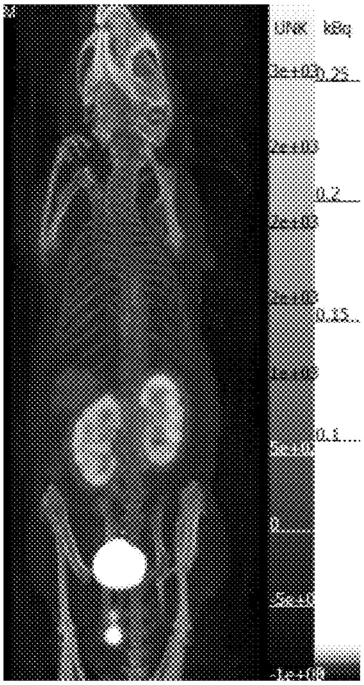
FIG. 13 shows an SPECT/CT image of $^{99m}$Tc-HYNIC/EDDA-PSMA-XL-3 imaging under the PC-3 tumor model.

1 mCi/0.2 ml of the $^{99m}$Tc-HYNIC/EDDA-PSMA-XL-2 or $^{99m}$Tc-HYNIC/EDDA-PSMA-XL-3 complex was injected into tail vein of the tumor-bearing mice. 2 hours after injection, the experimental animals were imaged with Small-Animal SPECT/CT. The images were shown in FIGS. 12 and 13.

Embodiment 11

In Vivo Distribution Study in Mice Under the Prostate Tumor Model

Male SCID mice weighing 18-20 g, were provided by SHANGHAI SLAC LABORATORY ANIMAL CO. LTD, and were raised in the SPF class animal laboratory of the Laboratory Animal Department of Fudan University. After two days of adaptive feeding in the animal room, LNCaP human prostate cancer cells were injected subcutaneously into the armpit of nude mice with an injection volume of 0.2 ml ($1\times10^7$ cells/ml dispersed in a 50% Matrigel). The feeding was continued for 4-6 weeks after injection, and the mice were used for in vivo distribution experiments when the solid tumor mass grows to 500-600 $mm^3$.

Figure 14:
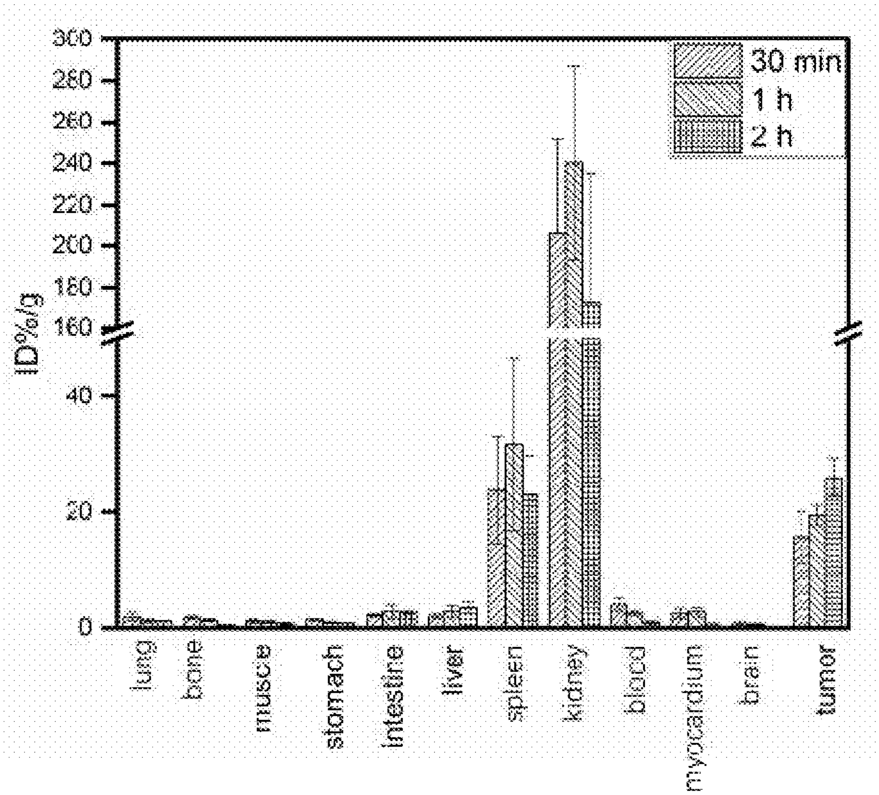
FIG. 14 shows the in vivo distribution of $^{99m}$Tc-HYNIC/EDDA-PSMA-XL-3 under the LNCaP tumor model.

20 μCi/0.2 ml of the $^{99m}$Tc-HYNIC/EDDA-PSMA-XL-3 complex was injected into tail vein of tumor-bearing mice. 0.5, 1 and 2 hours after injection, the mice were sacrificed under anesthesia and dissected. Each organ tissue was weighed, and the radioactivity was measured to calculate the drug uptake of each tissue. The results were shown in FIG. 14.

Embodiment 12

Preparation of $^{99m}$Tc-HYNIC-PSMA-XL-3 Lyophilized Kit:

1 mg of HYNIX-PSMA-XL-3, 1 g of disodium succinate, 0.3 g of succinic acid, 1 g of Tricine, 0.5 g of EDDA and 10 mg of $SnCl_2$ were dissolve in sterile water for injection, and metered to 100 ml. The mixture solution was sterilized by a sterile Millipore filter for subsequent packaging.

1 ml of the above solution was taken and placed in a 10 ml of sterile vial for split charging into 100 vials, then lyophilized in nitrogen atmosphere, and finally sealed for preservation.

Lyophilized kits were randomly selected and tested the sterility and bacterial endotoxin.

Embodiment 13

$^{99m}$Tc-HYNIC-PSMA-XL-3 for Human Use 30-100 mCi of $Na^{99m}TcO_4$ solution was added to a vial of $^{99m}$Tc-HYNIC-PSMA-XL-3 lyophilized kit, and reacted at 100° C. for 10 min. The radiochemical purity of $^{99m}$Tc-HYNIX-PSMA-XL-3 was determined by radio-TLC. Radionuclide purity was controlled by half-life measurements as well as gamma spectroscopy. The pH, clarity, radioactive concentration, as well as sterility and bacterial endotoxin of product solution were tested.

Embodiment 14

Application of $^{99m}$Tc-HYNIX-PSMA-XL-3 in Patients with Prostate Cancer.

Figure 15:
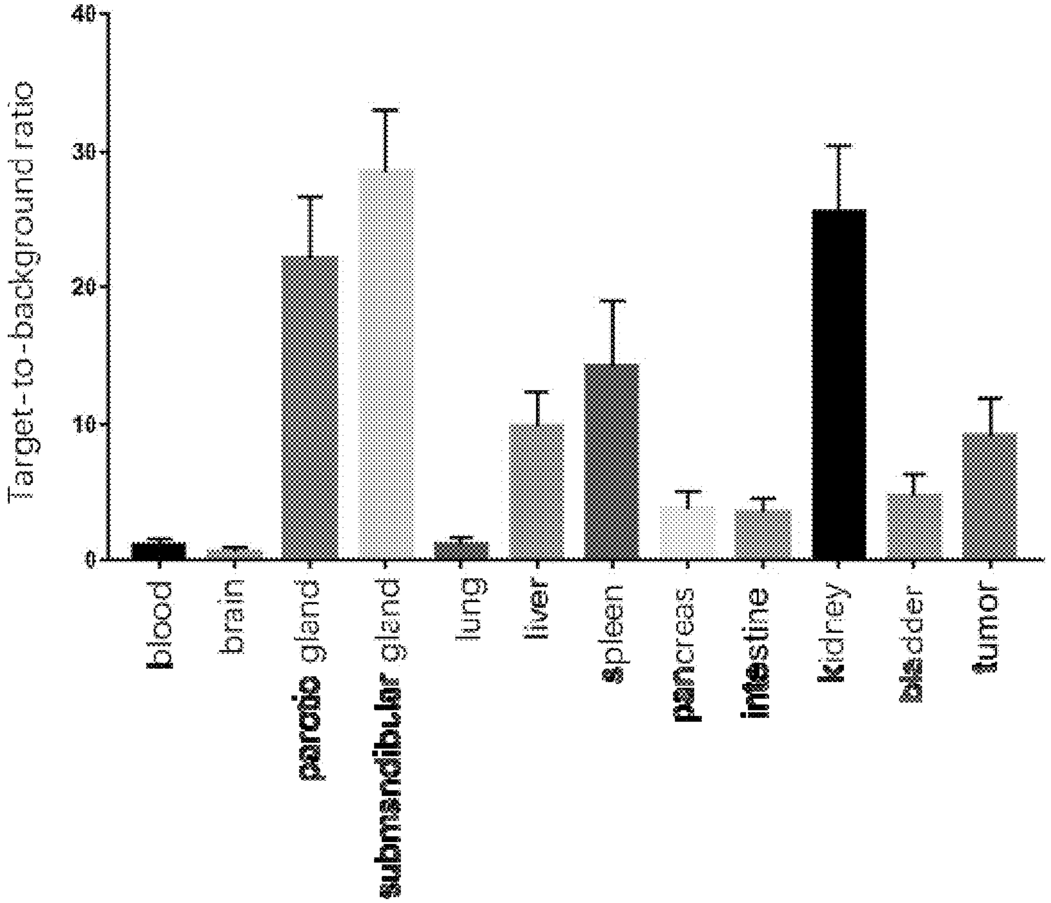
FIG. 15 shows a target-to-background ratio (TBR) image of different tissues undergoing SPECT/CT imaging after injection of $^{99m}$Tc-HYNIC-PSMA-XL-3 into a prostate cancer patient.
Figure 16:
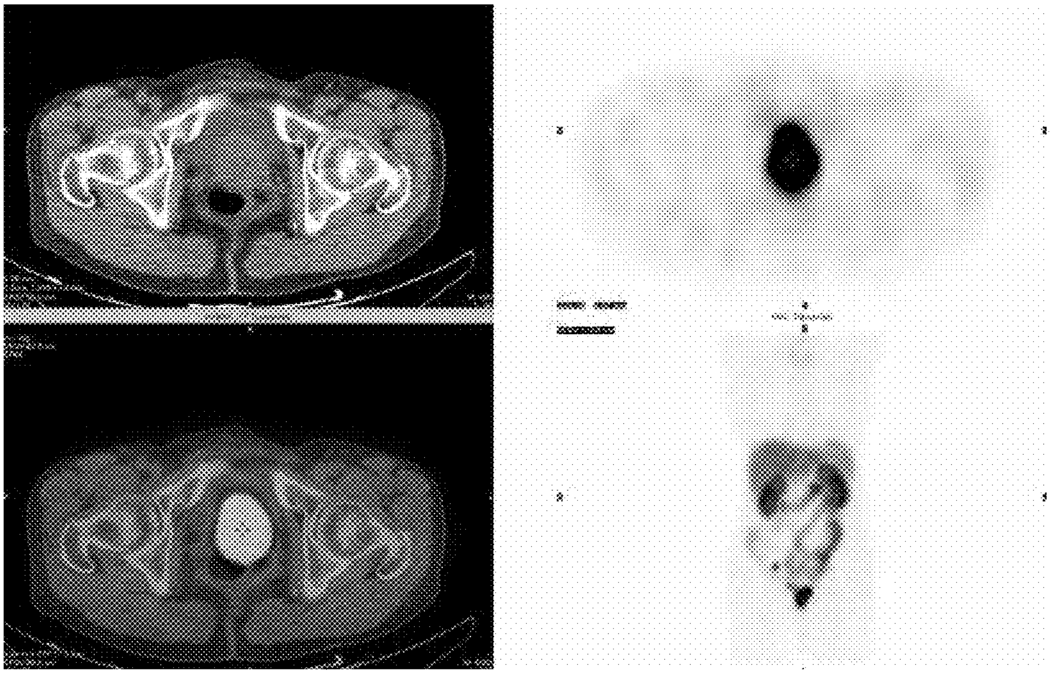
FIG. 16 shows typical images of SPECT/CT imaging after injection of $^{99m}$Tc-HYNIC-PSMA-XL-3 into a patient with primary prostate cancer.
Figure 17:
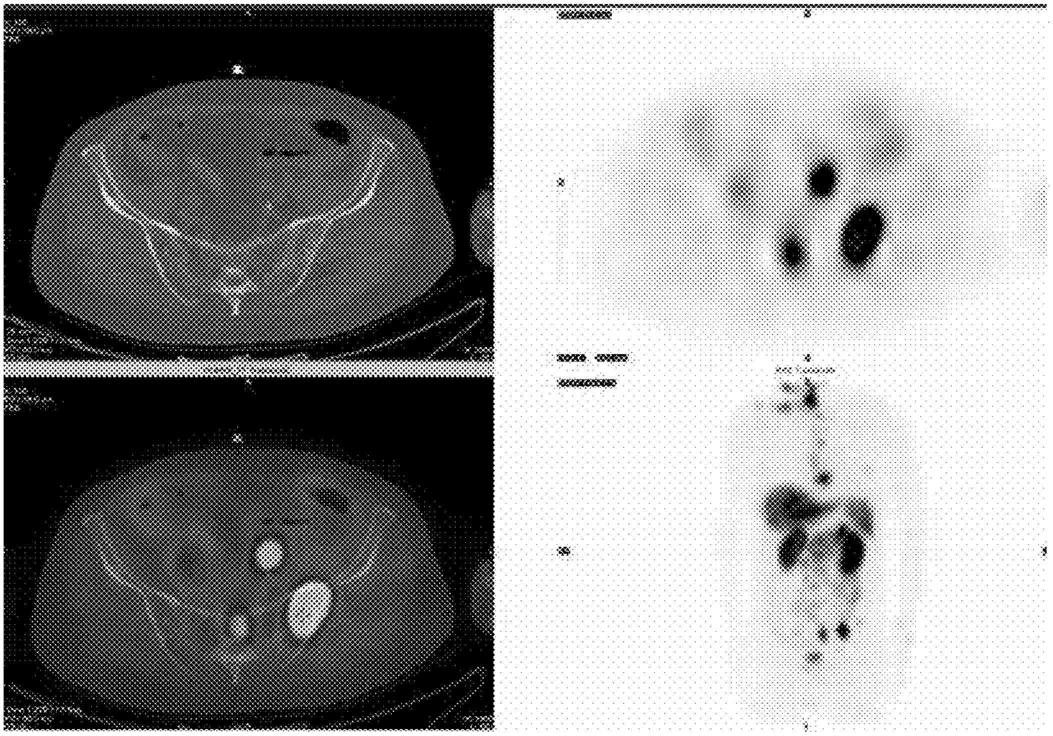
FIG. 17 shows typical images of SPECT/CT imaging after injection of $^{99m}$Tc-HYNIC-PSMA-XL-3 into a prostate cancer patient with multiple systemic metastases.

SPECT/CT imaging was performed on 10 patients with prostate cancer, including 5 patients with primary prostate cancer, 3 patients with biochemical recurrence, and 2 patients with hormone-resistant prostate cancer. The specific clinical information was shown in Table 3. The patients were injected with about 740MBq of $^{99m}$Tc-HYNIC-PSMA-XL-3, and 2 hours later, they were examined by a Discovery 670 (GE, USA) scanner. Taking the right obturator internus muscle as the background, the target-to-background ratio (TBR) was calculated, and the results were shown in FIG. 15. It can be seen that the distribution of radioactivity in the bladder is low, which is significantly lower than the tumor uptake, indicating excellent diagnostic performance for the primary tumors. A typical example was shown in FIG. 16. In addition, the tumor targeting is high and has a superior detection value for metastases such as lymph nodes/bone. A typical example was shown in FIG. 17.

TABLE 3

Clinical characteristics of 10 patients with prostate cancer

| No. | Age | Pathology of primary tumors | Gleason Score | State | PSA value before imaging (ng/ml) | Tumor location |
|---|---|---|---|---|---|---|
| 1 | 77 | acinar adenocarcinoma (puncture) | 5 + 4 | before treatment | 9.9 | prostate |
| 4 | 56 | acinar adenocarcinoma (puncture) | 4 + 3 | before treatment | 15.23 | prostate |
| 5 | 71 | ductal adenocarcinoma (puncture) | 4 + 3 | before treatment | 27.82 | prostate + pelvic lymph nodes |
| 6 | 68 | acinar adenocarcinoma (puncture) | 4 + 4 | before treatment | 18.22 | prostate + pelvic lymph nodes |
| 2 | 62 | acinar adenocarcinoma (puncture) | 3 + 4 | before treatment | 34.8 | prostate + multiple lymph nodes + bone |
| 3 | 80 | acinar adenocarcinoma (radical surgery) | 5 + 4 | biochemical recurrence | 0.78 | T12 + L5 vertebral body |
| 7 | 72 | acinar adenocarcinoma (radical surgery) | 4 + 5 | biochemical recurrence | 1.22 | prostatic fossa |
| 8 | 69 | acinar adenocarcinoma (radical surgery) | 4 + 4 | biochemical recurrence | 7.78 | right iliac blood vessels |
| 9 | 59 | acinar adenocarcinoma (radical surgery) | 4 + 5 | hormone resistance period | 34.91 | multiple bones |
| 10 | 70 | ductal adenocarcinoma (puncture) | 5 + 5 | hormone resistance period | 12.56 | lymph node + bone |

Figure 18:
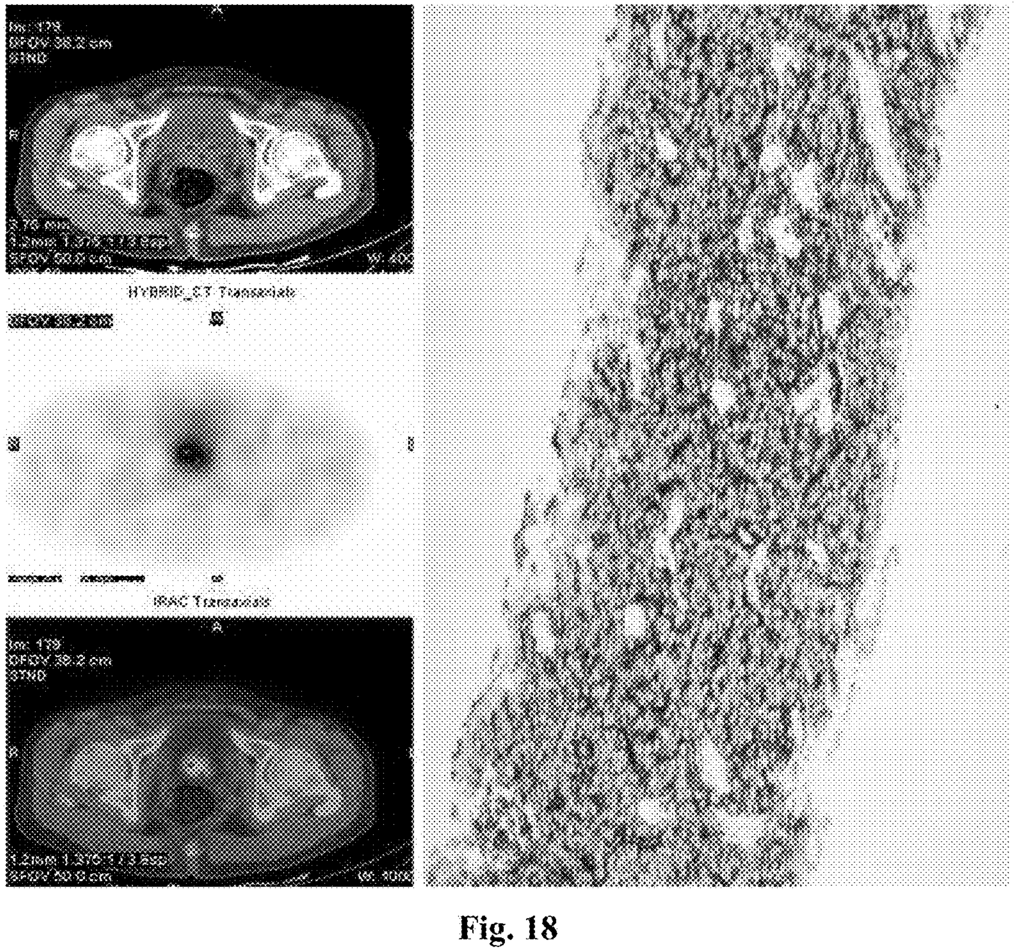
FIG. 18 shows pictures of $^{99m}$Tc-HYNIC-PSMA-XL-3 SPECT/CT imaging tumors and corresponding immunohistochemical pictures of surgical specimens in a prostate cancer patient. The results show that the $^{99m}$Tc-HYNIC-PSMA-XL-3 SPECT/CT imaging tumors in a prostate cancer patient were highly consistent with the immunohistochemical PSMA expression of the corresponding surgical specimens.

Four of the five patients with primary prostate cancer underwent radical prostatectomy, and one of the three patients with biochemical recurrence prostate cancer underwent salvage lymph node dissection. Without knowing the results of $^{99m}$Tc-HYNIC-PSMA-XL-3 SPECT/CT, pathology specialists performed pathological analysis of samples. Representative sections were stained by immunohistochemistry method, deparaffinized in xylene and rehydrated in graded ethanol series. Antigen retrieval was performed with the aid of autoclave and retrieval buffer (Target Retrieval Solution, Dako). Mouse monoclonal antibody against PSMA (clone 3E6, Dako) was diluted at a 1:100 dilution and incubated overnight at 4° C., followed by immunodetection using the Histostain-Plus Detection Kit (Invitrogen). Stained sections were scanned using Nanozoomer 2.0-HT Scansystem (Hamamatsu Photonics) to generate digital overall images. Pathological PSMA expression was consistent with high uptake tumors in SPECT/CT, and a typical case was shown in FIG. 18.

Embodiment 15

Figure 19:
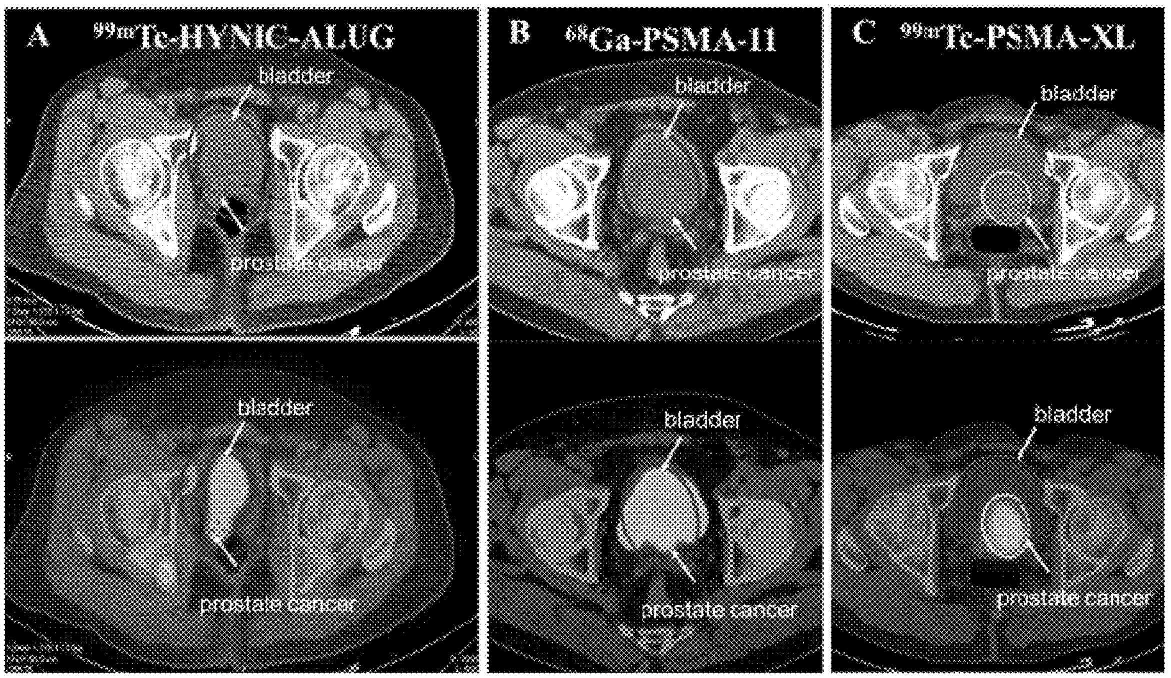
FIG. 19 shows primary tumors of a prostate cancer patient. The commonly used PSMA molecular probes $^{99m}$Tc-HYNIC-ALUG and $^{68}$Ga-PSMA11 in clinic both have high physiological distributions in the bladder (A/B in FIG. 19), which affects the distinction between prostate tumors and bladder physiological regions. However, the $^{99m}$Tc-HYNIC-PSMA-XL-3 of the present invention has a less distribution of radioactivity in the bladder (C in FIG. 19), therefore, distinguishing prostate cancer tumors from normal tissue structures clearly is achieved, and laying the foundation for further clinical puncture, surgery and other applications.

Comparative Study of $^{99m}$Tc-HYNIC-PSMA-XL-3 and Existing PSMA Imaging Agents that Commonly Used in Clinic 15 patients with prostate cancer were randomly divided into 3 groups. One group underwent $^{99m}$Tc-HYNIC-ALUG SPECT/CT, one group underwent $^{68}$Ga-PSMA11 PET/CT, and one group underwent $^{99m}$Tc-HYNIC-PSMA-XL3 SPECT/CT. The results showed that the bladders imaged by $^{99m}$Tc-HYNIC-ALUG SPECT/CT and $^{68}$Ga-PSMA11 PET/CT both exhibited a higher radiophysiological distribution (as shown in A and B of FIG. 19), which affected the distinction between prostate tumors and bladder physiological regions. In contrast, the bladders imaged by $^{99m}$Tc-HYNIC-PSMA-XL3 SPECT/CT exhibited a very low distribution of radioactivity (as shown in C of FIG. 19), which can clearly distinguish prostate tumors from normal tissue structures, laying the foundation for further clinical puncture, surgery and other applications.

Embodiment 16

Comparison of $^{99m}$Tc-HYNIC-PSMA-XL-3 SPECT/CT and $^{68}$Ga-PSMA11 PET/CT 10 patients with biochemical recurrent prostate cancer were randomly divided into two groups. The basic clinical information of the two groups was similar: they both have previously received radical prostatectomy, and the current PSA of them were 1-3 ng/ml, and the GS score of them were 8-9. One group underwent $^{68}$Ga-PSMA11 PET/CT, and the other group underwent $^{99m}$Tc-PSMA-XL SPECT/CT.

TABLE 4

Clinical characteristics and examination methods of 10 patients with prostate cancer

| No. | PSA | GS | Examination method | Number of tumors | With or without local recurrence |
|---|---|---|---|---|---|
| 1 | 1.2 | 8 | $^{68}$Ga-PSMA11 | 2 | no |
| 2 | 2.2 | 8 | $^{68}$Ga-PSMA11 | 1 | no |
| 3 | 2.5 | 9 | $^{68}$Ga-PSMA11 | 4 | yes |
| 4 | 0.8 | 8 | $^{68}$Ga-PSMA11 | 0 | no |
| 5 | 1.7 | 9 | $^{68}$Ga-PSMA11 | 1 | no |
| 6 | 2.4 | 9 | $^{99m}$Tc-PSMA-XL | 3 | yes |
| 7 | 0.6 | 8 | $^{99m}$Tc-PSMA-XL | 1 | no |
| 8 | 2.1 | 8 | $^{99m}$Tc-PSMA-XL | 2 | no |
| 9 | 1.6 | 8 | $^{99m}$Tc-PSMA-XL | 0 | no |
| 10 | 0.7 | 9 | $^{99m}$Tc-PSMA-XL | 4 | no |

After the preliminary statistics of the 10 patients, the positive rates of $^{68}$Ga-PSMA11 and $^{99m}$Tc-PSMA-XL imaging were both 80%, and at the same time, 1 patient in both $^{68}$Ga-PSMA11 and $^{99m}$Tc-PSMA-XL imaging were found to have local recurrence in the prostatic fossa. $^{99m}$Tc-PSMA-XL imaging is not inferior to $^{68}$Ga-PSMA11 imaging, which will be supported by designating prospective randomized controlled clinical trials and expanding the sample size in the future.

The meanings of the English abbreviations herein were shown in Table 5:

| English abbreviations | Chinese full names | English full names |
|---|---|---|
| Glu | 谷氨酸 | Glutamic acid |
| Lys | 赖氨酸 | Lysine |
| 2Nal | 2-氨基-3-奈基-丙酸 | 2-amino-3-(naphthalen-2-yl)propanoic acid |
| AMB | 4-氨基苯甲酸 | 4-aminobenzoic acid |
| HYNIC | 6-肼基烟酸 | 6-HYDRAZINONICOTINIC ACID |
| PSMA | 前列腺特异性膜抗原 | Prostate Specific Membrane Antigen |
| EDDA | 乙二胺-N,N'-二乙酸 | Ethylenediamine-N,N'-diacetic acid |
| TPPTS | 三苯基膦三间磺酸钠 | Triphenylphosphine-3,3',3''-trisulfonic acid trisodium |
| 2-PM PA | | 2-(Phosphonomethyl)pentanedioic acid |
| PSMA11 | They are all PSMA inhibitors synthesized based on Glu-Urea-Lys structure | |
| $^{19}$F-PSMA1007 | | |
| HYNIC-ALUG | | |

Embodiments of the present invention are described herein, comprising the preferred mode of the present invention known to the inventors. After reading the foregoing description, variations of those embodiments may become apparent to those skilled in the art. The inventors expect that those skilled in the art can suitably utilize such variations, and the present invention can be implemented differently from that described herein. Thus, as permitted by law, the present invention includes all variations and equivalents of the subject matter described in the claims. Moreover, unless otherwise indicated herein or otherwise obviously contradictory to the context, the elements described above in any combination of all possible modifications are included in the present invention.

What is claimed is:

1. A compound of formula (I-1) or a pharmaceutically acceptable salt, prodrug or ester thereof, wherein the formula (I-1) is:

formula (I-1)

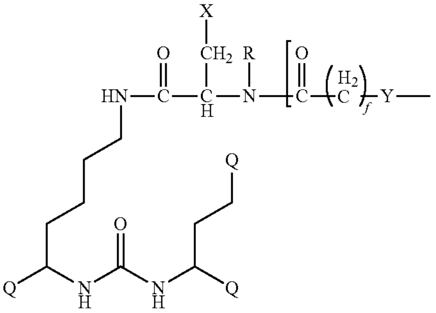

-continued

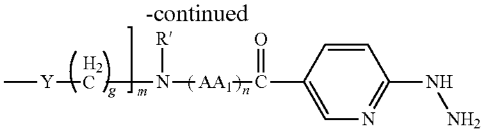

wherein:

m is 1;

n is 1;

f and g each is 0 or 1;

R and R' each is independently selected from H and alkyl;

Q is —COOH;

X is naphthyl, which is optionally substituted by at least one R group;

Y is phenyl, which is optionally substituted by at least one R group;

$AA_1$ is

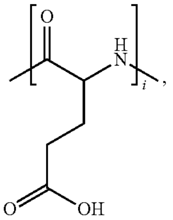

wherein i=1-3.

2. The compound of formula (I-1) or the pharmaceutically acceptable salt, prodrug or ester thereof according to claim 1, wherein:

the R and R' each is independently selected from H and $C_1$-$C_{10}$ alkyl.

3. The compound according to claim 1, having the following structures:

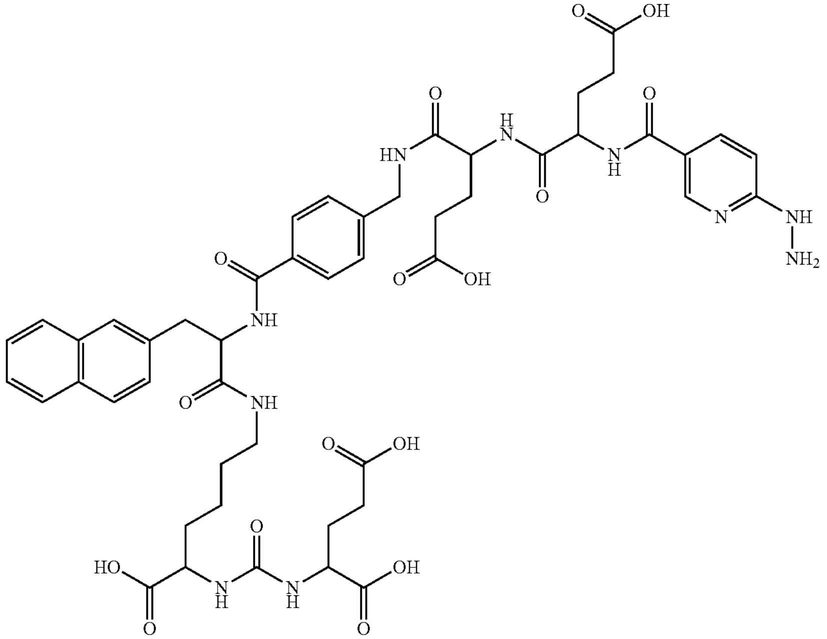

or

-continued
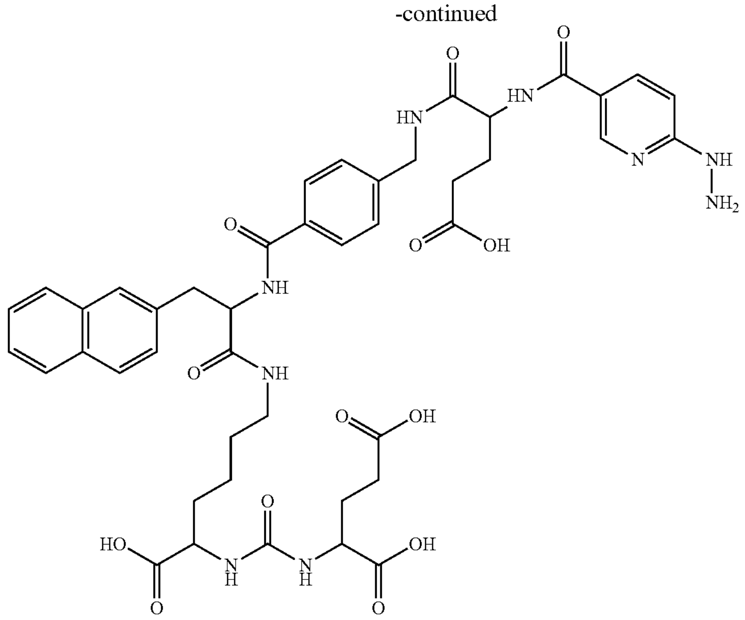
4. A $^{99m}$Tc complex of the compound of formula (I-1) according to claim 1, having a structure of formula (II-1):
formula (II-1)
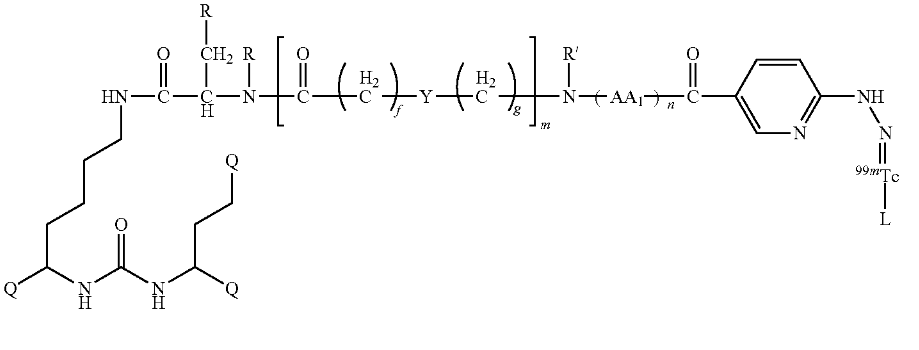

wherein Q, R, X, f, Y, g, m, R', $AA_1$ and n are as defined in claim 1, and L comprises one or more of N-tris(hydroxymethyl) methylglycine, ethylenediamine-N,N'-diacetic acid, triphenylphosphine-3,3',3"-trisulfonic acid trisodium, disodium 3,3'-(phenylphosphinediyl)bis(benzene-1-sulphonate), sodium diphenylphosphinobenzene-3-sulfonate, nicotinic acid, glucoheptonate, glucosamine, mannitol, and diphenylphosphinobenzoic acid.

5. The $^{99m}$Tc complex according to claim 4, wherein: the R and R' each is independently selected from H and $C_1$-$C_{10}$ alkyl.

6. The $^{99m}$Tc complex according to claim 4, wherein the $^{99m}$Tc complex is selected from the following compounds:

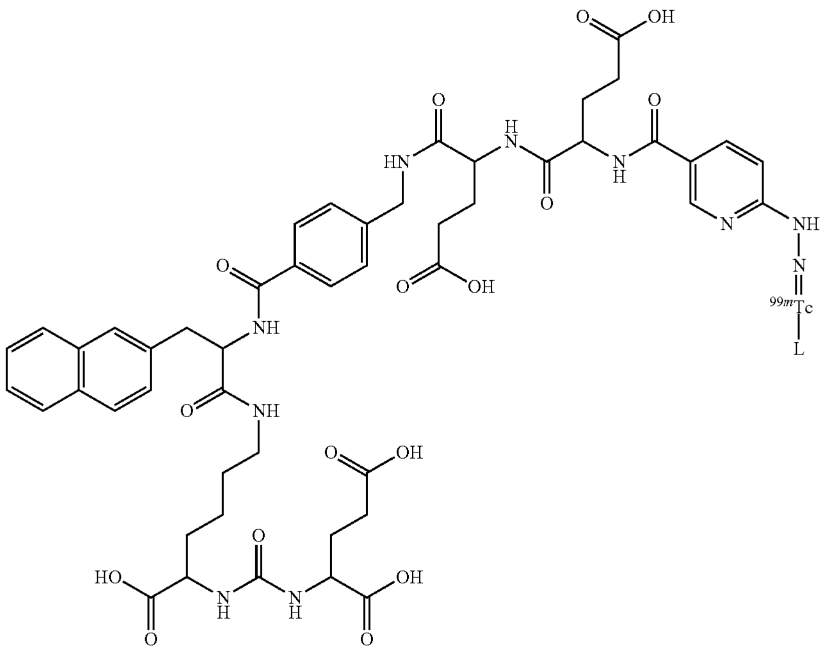

or

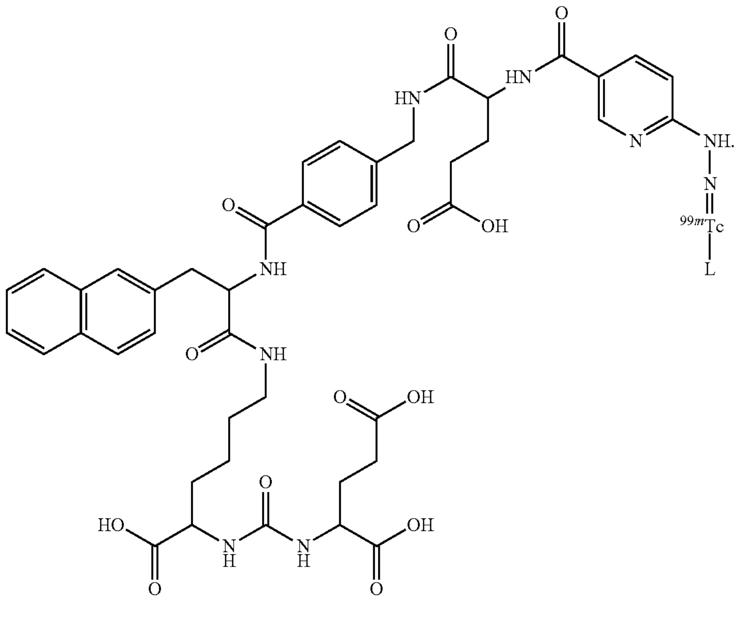

7. A preparation method of the $^{99m}$Tc complex according to claim 4, comprising:

formulating 0.5-2 ml of a mixture containing 1-100 ug of the compound according to claim 1, 0-500 μg of stannous chloride, 1-50 mg of a ligand L, 20-50 mg of disodium succinate, 5-30 mg of succinic acid, and 0-100 mg of mannitol in a 10-mL vial; adding 0.5-2 mL of $Na^{99m}TcO_4$ solution 10-100 mCi;

heating the vial in a 100° C. water bath to carry out reaction for 10-20 minutes; and cooling at room temperature for 10 minutes after the reaction is completed; thus obtaining the $^{99m}$Tc complex according to claim 6;

wherein the ligand L is selected from N-tris(hydroxymethyl)methylglycine, ethylenediaminediacetic acid, triphenylphosphine-3,3',3"-trisulfonate, disodium 3,3'-(phenylphosphinediyl)bis(benzene-1-sulphonate), sodium diphenylphosphinobenzene-3-sulfonate, nicotinic acid, glucoheptonate, glucosamine, mannitol, or diphenylphosphinobenzoic acid.

8. A pharmaceutical composition comprising the compound according to claim 1, or the pharmaceutically acceptable salt, prodrug or ester thereof, and a pharmaceutically acceptable carrier.

9. A method for imaging in a patient, comprising:

administrating an effective amount of the compound according to claim 1 to a subject in need thereof.

10. A method for diagnosing prostate cancer and/or its metastases, comprising:

administrating an effective amount of the compound according to claim 1 to a subject in need thereof.

11. A pharmaceutical composition comprising the $^{99m}$Tc complex according to claim 4, or the pharmaceutically acceptable salt, prodrug or ester thereof, and a pharmaceutically acceptable carrier.

12. A method for imaging in a patient, comprising:

administrating an effective amount of the $^{99m}$Tc complex according to claim 4 to a subject in need thereof.

13. A method for diagnosing prostate cancer and/or its metastases, comprising:

administrating an effective amount of the $^{99m}$Tc complex according to claim 4 to a subject in need thereof.

* * * * *